United States Patent [19]

Hagopian et al.

[11] Patent Number: 5,547,847
[45] Date of Patent: Aug. 20, 1996

[54] DIAGNOSIS OF INSULIN-DEPENDENT DIABETES

[75] Inventors: William Hagopian, Seattle, Wash.; Ake Lernmark, Malmo, Sweden; Allan E. Karlsen, Allerød, Denmark; Mona Landin-Olsson, Lund, Sweden

[73] Assignee: University of Washington, Seattle, Wash.

[21] Appl. No.: 117,907

[22] Filed: Sep. 7, 1993

[51] Int. Cl.⁶ .................................................. G01N 33/573
[52] U.S. Cl. ........................... 435/7.4; 435/7.5; 435/7.6; 435/7.92; 436/506; 436/518; 436/811
[58] Field of Search ............................. 435/7.4, 7.5, 7.6, 435/7.92; 436/506, 518, 811

[56] References Cited

U.S. PATENT DOCUMENTS 5,200,318  4/1993  Rabin et al. .......................... 435/7.21

FOREIGN PATENT DOCUMENTS

92/21979  12/1992  WIPO .

OTHER PUBLICATIONS

Karlsen et al., Cloning and Primary Structure of a Human Islet Isoform of Glutomic Acid Decarboxylase from Chromosome 10. Proc. Natl. Acad. Sci. 88: 8337–8341, 1991.

Hagopian et al., *J. Clin. Invest.* 91: 368–374, 1993.
Tuomi et al., *Diabetes* 42: 359–362, 1993.
Rowley et al., *Diabetes* 41: 548–551, 1992.
Kobayashi et al., *Diabetes* 36: 510–517, 1987.
Nakanishi et al., *Diabetes Res.* 9: 105–109, 1988.
Benhamou et al., *Clin. Nephrol.* 38: 239–244, 1992.
Landin–Olsson et al., *Diabetologia* 33: 561–568, 1990.
Harrison, *Immunol. Today* 13: 348–352, 1992.
Mauch et al., *Eur. J. Biochem.* 212: 597–603, 1993.
Neifing et al.,*Metabolism* 42: 482–486, 1993.
Thivolet et al., Diabetologia 35: 570–576, 1992.

*Primary Examiner*—Toni R. Scheiner
*Assistant Examiner*—Donna C. Wortman
*Attorney, Agent, or Firm*—Gary E. Parker; Debra K. Leith; Deborah A. Sawislak

[57] ABSTRACT

Methods for predicting the clinical course of diabetes in patients diagnosed as having NIDDM are provided. Patients having NIDDM are tested for the presence of autoantibodies to human islet cell glutamic acid decarboxylase. Based on the presence or absence of autoantibodies, the patients are classified as to the predicted course of the disease. These methods can be used to predict the development of IDDM and to guide therapeutic intervention.

20 Claims, 5 Drawing Sheets

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
    ( A ) LENGTH: 2370 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 38..1792

( x i ) SEQUENCE DESCRIPTION: SEQ ID NO:1:

```
GGCACTCGCT GGCGACCTGC TCCAGTCTCC AAAGCCG ATG GCA TCT CCG GGC TCT         55
                                        Met Ala Ser Pro Gly Ser
                                        1               5

GGC TTT TGG TCT TTC GGG TCG GAA GAT GGC TCT GGG GAT TCC GAG AAT        103
Gly Phe Trp Ser Phe Gly Ser Glu Asp Gly Ser Gly Asp Ser Glu Asn
        10                  15                  20

CCC GGC ACA GCG CGA GCC TGG TGC CAA GTG GCT CAG AAG TTC ACG GGC        151
Pro Gly Thr Ala Arg Ala Trp Cys Gln Val Ala Gln Lys Phe Thr Gly
            25                  30                  35

GGC ATC GGA AAC AAA CTG TGC GCC CTG CTC TAC GGA GAC GCC GAG AAG        199
Gly Ile Gly Asn Lys Leu Cys Ala Leu Leu Tyr Gly Asp Ala Glu Lys
    40                  45                  50

CCG GCG GAG AGC GGC GGG AGC CAA CCC CCG CGG GCC GCC GCC CGG AAG        247
Pro Ala Glu Ser Gly Gly Ser Gln Pro Pro Arg Ala Ala Ala Arg Lys
55                  60                  65                  70

GCC GCC TGC GCC TGC GAC CAG AAG CCC TGC AGC TGC TCC AAA GTG GAT        295
Ala Ala Cys Ala Cys Asp Gln Lys Pro Cys Ser Cys Ser Lys Val Asp
                75                  80                  85

GTC AAC TAC GCG TTT CTC CAT GCA ACA GAC CTG CTG CCG GCG TGT GAT        343
Val Asn Tyr Ala Phe Leu His Ala Thr Asp Leu Leu Pro Ala Cys Asp
            90                  95                  100

GGA GAA AGG CCC ACT TTG GCG TTT CTG CAA GAT GTT ATG AAC ATT TTA        391
Gly Glu Arg Pro Thr Leu Ala Phe Leu Gln Asp Val Met Asn Ile Leu
        105                 110                 115

CTT CAG TAT GTG GTG AAA AGT TTC GAT AGA TCA ACC AAA GTG ATT GAT        439
Leu Gln Tyr Val Val Lys Ser Phe Asp Arg Ser Thr Lys Val Ile Asp
    120                 125                 130

TTC CAT TAT CCT AAT GAG CTT CTC CAA GAA TAT AAT TGG GAA TTG GCA        487
Phe His Tyr Pro Asn Glu Leu Leu Gln Glu Tyr Asn Trp Glu Leu Ala
135                 140                 145                 150

GAC CAA CCA CAA AAT TTG GAG GAA ATT TTG ATG CAT TGC CAA ACA ACT        535
Asp Gln Pro Gln Asn Leu Glu Glu Ile Leu Met His Cys Gln Thr Thr
                155                 160                 165

CTA AAA TAT GCA ATT AAA ACA GGG CAT CCT AGA TAC TTC AAT CAA CTT        583
Leu Lys Tyr Ala Ile Lys Thr Gly His Pro Arg Tyr Phe Asn Gln Leu
            170                 175                 180

TCT ACT GGT TTG GAT ATG GTT GGA TTA GCA GCA GAC TGG CTG ACA TCA        631
Ser Thr Gly Leu Asp Met Val Gly Leu Ala Ala Asp Trp Leu Thr Ser
        185                 190                 195

ACA GCA AAT ACT AAC ATG TTC ACC TAT GAA ATT GCT CCA GTA TTT GTG        679
Thr Ala Asn Thr Asn Met Phe Thr Tyr Glu Ile Ala Pro Val Phe Val
    200                 205                 210
```

| | | | | | | | | | | | | | | | | |
|---|---|---|---|---|---|---|---|---|---|---|---|---|---|---|---|---|
| CTT | TTG | GAA | TAT | GTC | ACA | CTA | AAG | AAA | ATG | AGA | GAA | ATC | ATT | GGC | TGG | 727 |
| Leu | Leu | Glu | Tyr | Val | Thr | Leu | Lys | Lys | Met | Arg | Glu | Ile | Ile | Gly | Trp | |
| 215 | | | | 220 | | | | | 225 | | | | | 230 | | |
| CCA | GGG | GGC | TCT | GGC | GAT | GGG | ATA | TTT | TCT | CCC | GGT | GGC | GCC | ATA | TCT | 775 |
| Pro | Gly | Gly | Ser | Gly | Asp | Gly | Ile | Phe | Ser | Pro | Gly | Gly | Ala | Ile | Ser | |
| | | | | 235 | | | | 240 | | | | | | 245 | | |
| AAC | ATG | TAT | GCC | ATG | ATG | ATC | GCA | CGC | TTT | AAG | ATG | TTC | CCA | GAA | GTC | 823 |
| Asn | Met | Tyr | Ala | Met | Met | Ile | Ala | Arg | Phe | Lys | Met | Phe | Pro | Glu | Val | |
| | | | 250 | | | | | 255 | | | | | 260 | | | |
| AAG | GAG | AAA | GGA | ATG | GCT | GCT | CTT | CCC | AGG | CTC | ATT | GCC | TTC | ACG | TCT | 871 |
| Lys | Glu | Lys | Gly | Met | Ala | Ala | Leu | Pro | Arg | Leu | Ile | Ala | Phe | Thr | Ser | |
| | | 265 | | | | | 270 | | | | | 275 | | | | |
| GAA | CAT | AGT | CAT | TTT | TCT | CTC | AAG | AAG | GGA | GCT | GCA | GCC | TTA | GGG | ATT | 919 |
| Glu | His | Ser | His | Phe | Ser | Leu | Lys | Lys | Gly | Ala | Ala | Ala | Leu | Gly | Ile | |
| | 280 | | | | | 285 | | | | | 290 | | | | | |
| GGA | ACA | GAC | AGC | GTG | ATT | CTG | ATT | AAA | TGT | GAT | GAG | AGA | GGG | AAA | ATG | 967 |
| Gly | Thr | Asp | Ser | Val | Ile | Leu | Ile | Lys | Cys | Asp | Glu | Arg | Gly | Lys | Met | |
| 295 | | | | | 300 | | | | | 305 | | | | | 310 | |
| ATT | CCA | TCT | GAT | CTT | GAA | AGA | AGG | ATT | CTT | GAA | GCC | AAA | CAG | AAA | GGG | 1015 |
| Ile | Pro | Ser | Asp | Leu | Glu | Arg | Arg | Ile | Leu | Glu | Ala | Lys | Gln | Lys | Gly | |
| | | | | 315 | | | | | 320 | | | | | 325 | | |
| TTT | GTT | CCT | TTC | CTC | GTG | AGT | GCC | ACA | GCT | GGA | ACC | ACC | GTG | TAC | GGA | 1063 |
| Phe | Val | Pro | Phe | Leu | Val | Ser | Ala | Thr | Ala | Gly | Thr | Thr | Val | Tyr | Gly | |
| | | | 330 | | | | | 335 | | | | | 340 | | | |
| GCA | TTT | GAC | CCC | CTC | TTA | GCT | GTC | GCT | GAC | ATT | TGC | AAA | AAG | TAT | AAG | 1111 |
| Ala | Phe | Asp | Pro | Leu | Leu | Ala | Val | Ala | Asp | Ile | Cys | Lys | Lys | Tyr | Lys | |
| | | 345 | | | | | 350 | | | | | 355 | | | | |
| ATC | TGG | ATG | CAT | GTG | GAT | GCA | GCT | TGG | GGT | GGG | GGA | TTA | CTG | ATG | TCC | 1159 |
| Ile | Trp | Met | His | Val | Asp | Ala | Ala | Trp | Gly | Gly | Gly | Leu | Leu | Met | Ser | |
| | | | 360 | | | | 365 | | | | | 370 | | | | |
| CGA | AAA | CAC | AAG | TGG | AAA | CTG | AGT | GGC | GTG | GAG | AGG | GCC | AAC | TCT | GTG | 1207 |
| Arg | Lys | His | Lys | Trp | Lys | Leu | Ser | Gly | Val | Glu | Arg | Ala | Asn | Ser | Val | |
| 375 | | | | | 380 | | | | | 385 | | | | | 390 | |
| ACG | TGG | AAT | CCA | CAC | AAG | ATG | ATG | GGA | GTC | CCT | TTG | CAG | TGC | TCT | GCT | 1255 |
| Thr | Trp | Asn | Pro | His | Lys | Met | Met | Gly | Val | Pro | Leu | Gln | Cys | Ser | Ala | |
| | | | | 395 | | | | | 400 | | | | | 405 | | |
| CTC | CTG | GTT | AGA | GAA | GAG | GGA | TTG | ATG | CAG | AAT | TGC | AAC | CAA | ATG | CAT | 1303 |
| Leu | Leu | Val | Arg | Glu | Glu | Gly | Leu | Met | Gln | Asn | Cys | Asn | Gln | Met | His | |
| | | | 410 | | | | | 415 | | | | | 420 | | | |
| GCC | TCC | TAC | CTC | TTT | CAG | CAA | GAT | AAA | CAT | TAT | GAC | CTG | TCC | TAT | GAC | 1351 |
| Ala | Ser | Tyr | Leu | Phe | Gln | Gln | Asp | Lys | His | Tyr | Asp | Leu | Ser | Tyr | Asp | |
| | | 425 | | | | | 430 | | | | | 435 | | | | |
| ACT | GGA | GAC | AAG | GCC | TTA | CAG | TGC | GGA | CGC | CAC | GTT | GAT | GTT | TTT | AAA | 1399 |
| Thr | Gly | Asp | Lys | Ala | Leu | Gln | Cys | Gly | Arg | His | Val | Asp | Val | Phe | Lys | |
| | | 440 | | | | | 445 | | | | | 450 | | | | |
| CTA | TGG | CTG | ATG | TGG | AGG | GCA | AAG | GGG | ACT | ACC | GGG | TTT | GAA | GCG | CAT | 1447 |
| Leu | Trp | Leu | Met | Trp | Arg | Ala | Lys | Gly | Thr | Thr | Gly | Phe | Glu | Ala | His | |
| 455 | | | | | 460 | | | | | 465 | | | | | 470 | |
| GTT | GAT | AAA | TGT | TTG | GAG | TTG | GCA | GAG | TAT | TTA | TAC | AAC | ATC | ATA | AAA | 1495 |
| Val | Asp | Lys | Cys | Leu | Glu | Leu | Ala | Glu | Tyr | Leu | Tyr | Asn | Ile | Ile | Lys | |
| | | | | 475 | | | | | 480 | | | | | 485 | | |
| AAC | CGA | GAA | GGA | TAT | GAG | ATG | GTG | TTT | GAT | GGG | AAG | CCT | CAG | CAC | ACA | 1543 |
| Asn | Arg | Glu | Gly | Tyr | Glu | Met | Val | Phe | Asp | Gly | Lys | Pro | Gln | His | Thr | |
| | | | 490 | | | | | 495 | | | | | 500 | | | |
| AAT | GTC | TGC | TTC | TGG | TAC | ATT | CCT | CCA | AGC | TTG | CGT | ACT | CTG | GAA | GAC | 1591 |
| Asn | Val | Cys | Phe | Trp | Tyr | Ile | Pro | Pro | Ser | Leu | Arg | Thr | Leu | Glu | Asp | |
| | | 505 | | | | | 510 | | | | | 515 | | | | |
| AAT | GAA | GAG | AGA | ATG | AGT | CGC | CTC | TCG | AAG | GTG | GCT | CCA | GTG | ATT | AAA | 1639 |
| Asn | Glu | Glu | Arg | Met | Ser | Arg | Leu | Ser | Lys | Val | Ala | Pro | Val | Ile | Lys | |
| | 520 | | | | | 525 | | | | | 530 | | | | | |

```
GCC  AGA  ATG  ATG  GAG  TAT  GGA  ACC  ACA  ATG  GTC  AGC  TAC  CAA  CCC  TTG    1687
Ala  Arg  Met  Met  Glu  Tyr  Gly  Thr  Thr  Met  Val  Ser  Tyr  Gln  Pro  Leu
535            540                      545                      550

GGA  GAC  AAG  GTC  AAT  TTC  TTC  CGC  ATG  GTC  ATC  TCA  AAC  CCA  GCG  GCA    1735
Gly  Asp  Lys  Val  Asn  Phe  Phe  Arg  Met  Val  Ile  Ser  Asn  Pro  Ala  Ala
               555                      560                      565

ACT  CAC  CAA  GAC  ATT  GAC  TTC  CTG  ATT  GAA  GAA  ATA  GAA  CGC  CTT  GGA    1783
Thr  His  Gln  Asp  Ile  Asp  Phe  Leu  Ile  Glu  Glu  Ile  Glu  Arg  Leu  Gly
               570                      575                      580

CAA  GAT  TTA  TAATAACCTT  GCTCACCAAG  CTGTTCCACT  TCTCTAGAGA                     1832
Gln  Asp  Leu
          585

ACATGCCCTC  AGCTAAGCCC  CCTACTGAGA  AACTTCCTTT  GAGAATTGTG  CGACTTCACA            1892

AAATGCAAGG  TGAACACCAC  TTTGTCTCTG  AGAACAGACG  TTACCAATTA  TGGAGTGTCA            1952

CCAGCTGCCA  AAATCGTAGG  TGTTGGCTCT  GCTGGTCACT  GGAGTAGTTG  CTACTCTTCA            2012

GAATATGGAC  AAAGAAGGCA  CAGGTGTAAA  TATAGTAGCA  GGATGAGGAA  CCTCAAACTG            2072

GGTATCATTT  GCACGTGCTC  TTCTGTTCTC  AAATGCTAAA  TGCAAACACT  GTGTATTTAT            2132

TAGTTAGGTG  TGCCAAACTA  CCGTTCCCAA  ATTGGTGTTT  CTGAATGACA  TCAACATTCC            2192

CCCAACATTA  CTCCATTACT  AAAGACAGAA  AAAAATAAAA  ACATAAAATA  TACAAACATG            2252

TGGCAACCTG  TTCTTCCTAC  CAAATATAAA  CTTGTGTATG  ATCCAAGTAT  TTTATCTGTG            2312

TTGTCTCTCT  AAACCCAAAT  AAATGTGTAA  ATGTGGACAC  AAAAAAAAAA  AAAAAAA              2370
```

(2) INFORMATION FOR SEQ ID NO:2:

(i) SEQUENCE CHARACTERISTICS:
       (A) LENGTH: 585 amino acids
       (B) TYPE: amino acid
       (D) TOPOLOGY: linear (ii) MOLECULE TYPE: protein (xi) SEQUENCE DESCRIPTION: SEQ ID NO:2:

```
Met  Ala  Ser  Pro  Gly  Ser  Gly  Phe  Trp  Ser  Phe  Gly  Ser  Glu  Asp  Gly
 1              5                   10                  15

Ser  Gly  Asp  Ser  Glu  Asn  Pro  Gly  Thr  Ala  Arg  Ala  Trp  Cys  Gln  Val
               20                  25                  30

Ala  Gln  Lys  Phe  Thr  Gly  Gly  Ile  Gly  Asn  Lys  Leu  Cys  Ala  Leu  Leu
               35                  40                  45

Tyr  Gly  Asp  Ala  Glu  Lys  Pro  Ala  Glu  Ser  Gly  Gly  Ser  Gln  Pro  Pro
 50                       55                       60

Arg  Ala  Ala  Ala  Arg  Lys  Ala  Ala  Cys  Ala  Cys  Asp  Gln  Lys  Pro  Cys
 65                       70                       75                       80

Ser  Cys  Ser  Lys  Val  Asp  Val  Asn  Tyr  Ala  Phe  Leu  His  Ala  Thr  Asp
                    85                  90                      95

Leu  Leu  Pro  Ala  Cys  Asp  Gly  Glu  Arg  Pro  Thr  Leu  Ala  Phe  Leu  Gln
               100                 105                     110

Asp  Val  Met  Asn  Ile  Leu  Leu  Gln  Tyr  Val  Val  Lys  Ser  Phe  Asp  Arg
          115                 120                 125

Ser  Thr  Lys  Val  Ile  Asp  Phe  His  Tyr  Pro  Asn  Glu  Leu  Leu  Gln  Glu
     130                      135                 140

Tyr  Asn  Trp  Glu  Leu  Ala  Asp  Gln  Pro  Gln  Asn  Leu  Glu  Glu  Ile  Leu
145                      150                 155                      160

Met  His  Cys  Gln  Thr  Thr  Leu  Lys  Tyr  Ala  Ile  Lys  Thr  Gly  His  Pro
               165                      170                     175

Arg  Tyr  Phe  Asn  Gln  Leu  Ser  Thr  Gly  Leu  Asp  Met  Val  Gly  Leu  Ala
```

```
              180                     185                     190
Ala  Asp  Trp  Leu  Thr  Ser  Thr  Ala  Asn  Thr  Asn  Met  Phe  Thr  Tyr  Glu
          195                     200                     205
Ile  Ala  Pro  Val  Phe  Val  Leu  Leu  Glu  Tyr  Val  Thr  Leu  Lys  Lys  Met
     210                     215                     220
Arg  Glu  Ile  Ile  Gly  Trp  Pro  Gly  Gly  Ser  Gly  Asp  Gly  Ile  Phe  Ser
225                      230                     235                      240
Pro  Gly  Gly  Ala  Ile  Ser  Asn  Met  Tyr  Ala  Met  Met  Ile  Ala  Arg  Phe
                    245                     250                     255
Lys  Met  Phe  Pro  Glu  Val  Lys  Glu  Lys  Gly  Met  Ala  Ala  Leu  Pro  Arg
               260                     265                     270
Leu  Ile  Ala  Phe  Thr  Ser  Glu  His  Ser  His  Phe  Ser  Leu  Lys  Lys  Gly
          275                     280                     285
Ala  Ala  Ala  Leu  Gly  Ile  Gly  Thr  Asp  Ser  Val  Ile  Leu  Ile  Lys  Cys
     290                     295                     300
Asp  Glu  Arg  Gly  Lys  Met  Ile  Pro  Ser  Asp  Leu  Glu  Arg  Arg  Ile  Leu
305                      310                     315                      320
Glu  Ala  Lys  Gln  Lys  Gly  Phe  Val  Pro  Phe  Leu  Val  Ser  Ala  Thr  Ala
                    325                     330                     335
Gly  Thr  Thr  Val  Tyr  Gly  Ala  Phe  Asp  Pro  Leu  Leu  Ala  Val  Ala  Asp
               340                     345                     350
Ile  Cys  Lys  Lys  Tyr  Lys  Ile  Trp  Met  His  Val  Asp  Ala  Ala  Trp  Gly
          355                     360                     365
Gly  Gly  Leu  Leu  Met  Ser  Arg  Lys  His  Lys  Trp  Lys  Leu  Ser  Gly  Val
     370                     375                     380
Glu  Arg  Ala  Asn  Ser  Val  Thr  Trp  Asn  Pro  His  Lys  Met  Met  Gly  Val
385                      390                     395                      400
Pro  Leu  Gln  Cys  Ser  Ala  Leu  Leu  Val  Arg  Glu  Glu  Gly  Leu  Met  Gln
                    405                     410                     415
Asn  Cys  Asn  Gln  Met  His  Ala  Ser  Tyr  Leu  Phe  Gln  Gln  Asp  Lys  His
               420                     425                     430
Tyr  Asp  Leu  Ser  Tyr  Asp  Thr  Gly  Asp  Lys  Ala  Leu  Gln  Cys  Gly  Arg
          435                     440                     445
His  Val  Asp  Val  Phe  Lys  Leu  Trp  Leu  Met  Trp  Arg  Ala  Lys  Gly  Thr
     450                     455                     460
Thr  Gly  Phe  Glu  Ala  His  Val  Asp  Lys  Cys  Leu  Glu  Leu  Ala  Glu  Tyr
465                      470                     475                      480
Leu  Tyr  Asn  Ile  Ile  Lys  Asn  Arg  Glu  Gly  Tyr  Glu  Met  Val  Phe  Asp
                    485                     490                     495
Gly  Lys  Pro  Gln  His  Thr  Asn  Val  Cys  Phe  Trp  Tyr  Ile  Pro  Pro  Ser
               500                     505                     510
Leu  Arg  Thr  Leu  Glu  Asp  Asn  Glu  Glu  Arg  Met  Ser  Arg  Leu  Ser  Lys
          515                     520                     525
Val  Ala  Pro  Val  Ile  Lys  Ala  Arg  Met  Met  Glu  Tyr  Gly  Thr  Thr  Met
     530                     535                     540
Val  Ser  Tyr  Gln  Pro  Leu  Gly  Asp  Lys  Val  Asn  Phe  Phe  Arg  Met  Val
545                      550                     555                      560
Ile  Ser  Asn  Pro  Ala  Ala  Thr  His  Gln  Asp  Ile  Asp  Phe  Leu  Ile  Glu
                    565                     570                     575
Glu  Ile  Glu  Arg  Leu  Gly  Gln  Asp  Leu
               580                     585
```

( 2 ) INFORMATION FOR SEQ ID NO:3:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: other nucleic acid ( v i i ) IMMEDIATE SOURCE:
    ( B ) CLONE: ZC3338

( x i ) SEQUENCE DESCRIPTION: SEQ ID NO:3:

GCGGGAGCGG ATCCTAATAC TACCAACCTG CG    32

( 2 ) INFORMATION FOR SEQ ID NO:4:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid ( v i i ) IMMEDIATE SOURCE:
        ( B ) CLONE: ZC3339

( x i ) SEQUENCE DESCRIPTION: SEQ ID NO:4:

ACCATGGTTG TTCCTGACTC CATCAT    26

( 2 ) INFORMATION FOR SEQ ID NO:5:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: other nucleic acid ( v i i ) IMMEDIATE SOURCE:
        ( B ) CLONE: ZC3337

( x i ) SEQUENCE DESCRIPTION: SEQ ID NO:5:

CTGACATCAA CTGCCAATAC CAATATGTTC ACATATGAAA TTGCA    45

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid ( v i i ) IMMEDIATE SOURCE:
        ( B ) CLONE: ZC3614

( x i ) SEQUENCE DESCRIPTION: SEQ ID NO:6:

AAATGAGAAT TCACACGCCG GCAGCAGGTC    30

( 2 ) INFORMATION FOR SEQ ID NO:7:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid (v i i) IMMEDIATE SOURCE:
    (B) CLONE: ZC3623

(x i) SEQUENCE DESCRIPTION: SEQ ID NO:7:

AAGGAATTCA AGTTGATTGA AGTATCT                                                  27

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: other nucleic acid (v i i) IMMEDIATE SOURCE:
        (B) CLONE: ZC3745

(x i) SEQUENCE DESCRIPTION: SEQ ID NO:8:

GGCGAATTCG CATATTTTAG AGTTGTTTGG                                                30

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: other nucleic acid (v i i) IMMEDIATE SOURCE:
        (B) CLONE: ZC3746

(x i) SEQUENCE DESCRIPTION: SEQ ID NO:9:

GGCGAATTCG GAGCAGCTGC AGGGCTTCTG                                                30

(2) INFORMATION FOR SEQ ID NO:10:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (i i) MOLECULE TYPE: other nucleic acid (v i i) IMMEDIATE SOURCE:
        (B) CLONE: ZC2633

(x i) SEQUENCE DESCRIPTION: SEQ ID NO:10:

AGGGAGACCG GAATTCGACT CGAGTCGACA TCGATCAG                                      38

(2) INFORMATION FOR SEQ ID NO:11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (i i) MOLECULE TYPE: other nucleic acid (v i i) IMMEDIATE SOURCE:
        (B) CLONE: ZC2488

(x i) SEQUENCE DESCRIPTION: SEQ ID NO:11:

GACTCGAGTC GACATCGATC AGCCCCCCCC CC                                            32

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:12:

GGCGATTAAG TTGGGTAA                                        18

( 2 ) INFORMATION FOR SEQ ID NO:13:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:13:

TAACAATTTC ACACAGG                                       17

( 2 ) INFORMATION FOR SEQ ID NO:14:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:14:

CCAGTCTGAA TTCACCATGC TAGCCCAGGC TCCGGAT              37

( 2 ) INFORMATION FOR SEQ ID NO:15:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:15:

TTTTAGAGAA GCTTGGCAAT GCATCAAAAT TTCCTCC              37

( 2 ) INFORMATION FOR SEQ ID NO:16:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:16:

Thr Gln Ser Asp Ile Asp Phe Leu Ile Glu Glu Ile Glu Arg Leu Gly
1                5                          10                      15

Gln Asp Leu ( 2 ) INFORMATION FOR SEQ ID NO:17:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:17:

Pro His Lys Met Met Gly
1           5

DIAGNOSIS OF INSULIN-DEPENDENT DIABETES

GOVERNMENT SUPPORT

This invention was made with government support under grant numbers DK17047, DK26190, DK33873, DK41801 and DK42654 awarded by the National Institutes of Health/ Juvenile Diabetes Foundation. The government has certain rights in the invention.

BACKGROUND OF THE INVENTION

Insulin-dependent diabetes mellitus (IDDM) is a disease resulting from the autoimmune destruction of the insulin-producing β-cells of the pancreas. Studies directed at identifying the autoantigen(s) responsible for β-cell destruction have identified several candidates, including insulin (Palmer et al., Science 222: 1337–1339 (1983)), a poorly characterized islet cell antigen (Bottazzo et al, Lancet ii: 1279–1283 (1974)) and a 64 kDa antigen that has been shown to be glutamic acid decarboxylase (Baekkeskov et al., Nature 298: 167–169 (1982); Baekkeskov et al., Nature 347: 151–156 (1990)). Antibodies to glutamic acid decarboxylase (hereinafter referred to as "GAD") have been found to be present in patients prior to clinical manifestation of IDDM (Baekkeskov et al, J. Clin. Invest. 79:926–934 (1987)).

GAD catalyzes the rate-limiting step in the synthesis of γ-aminobutyric acid (GABA), a major inhibitory neurotransmitter of the mammalian central nervous system. Little is known with certainty regarding the regulation of GAD activity or the expression of GAD genes. Despite its wide distribution in the brain, GAD protein is present in very small quantities and is very difficult to purify to homogeneity. GAD has multiple isoforms encoded by different genes. These multiple forms of the enzyme differ in molecular weight, kinetic properties, sequence (when known), and hydrophobic properties. For example, the presence of three different forms of GAD in porcine brain has been reported (Spink et al., J. Neurochem. 40:1113–1119 (1983)), as well as four forms in rat brain (Spink et al., Brain Res. 421:235–244 (1987)). A mouse brain GAD (Huang et al., Proc. Natl. Acad. Sci. USA 87:8491–8495 (1990)) and a GAD clone isolated from feline brain (Kobayashi et al., J. Neurosci. 7:2768–2772 (1987)) have also been reported. At least two isomers of GAD have been reported in human brain (Chang and Gottlieb, J. Neurosci. 8:2123–2130 (1988)). A human pancreatic islet cell GAD has recently been characterized by molecular cloning (Lernmark et al., U.S. patent application Ser. No. 07/702,162; PCT publication WO 92/20811). This form of GAD is identical to one subsequently identified human brain isoform (Bu et al., Proc. Natl. Acad. Sci. USA 89:2115–2119, 1992). A second GAD isoform identified in human brain is not present in human islets (Karlsen et al., Diabetes 41:1355–1359, 1992).

For at least the first decade of their disease, non-insulin-dependent diabetes (NIDDM) patients are generally treated with oral hypoglycemic agents and/or controlled diet. IDDM and classic NIDDM are generally agreed to have distinct pathegeneses, with only the former being autoimmune in nature. However, IDDM occurs more frequently in patients with a strong history of NIDDM than in the general population (Dahlquist et al., Diabetologia 32:2–6 (1989)), i.e. a significant population of NIDDM patients actually have autoimmune etiology and would be more accurately classified as IDDM. These patients eventually require insulin therapy. Since effective autoimmune intervention strategies for IDDM will probably exist soon, identification of autoimmune diabetes before clinical onset is critically important. Accurate classification of diabetes type may also guide glucoregulatory therapy. Furthermore, loss of functional islet cell mass is slowed in IDDM by treatment with exogenous insulin (Keller, Diabetes 41 (Suppl. 1), xvi, 1992). There is therefore a need in the art for methods of determining the presence of IDDM before clinical onset, including the diagnosis of incipient IDDM in individuals classified as NIDDM. The present invention provides such methods, as well as other, related advantages.

SUMMARY OF THE INVENTION

It is an object of the present invention to provide compositions and methods for predicting the clinical course of diabetes, particularly in patients diagnosed as having NIDDM.

Within one aspect, the present invention provides methods for predicting the clinical course of diabetes in a patient wherein a biological fluid from a patient diagnosed as having NIDDM is tested for the presence of autoantibodies to human islet cell GAD. The patient is then classified for clinical course of diabetes based on the presence or absence of the autoantibodies, the presence of the autoantibodies indicating that apparent NIDDM is actually IDDM. Within one embodiment of the invention, the patient is further tested for one or more additional diabetes-specific autoantibodies, fasting C-peptide level or body mass index. Within another embodiment, the step of testing comprises combining the biological fluid with labeled human islet cell GAD under conditions suitable for immune complex formation, separating immune complexes from uncomplexed GAD, and determining the presence of labeled GAD in the immune complexes.

Within another aspect, the present invention provides methods for determining the presence of autoantibodies to human islet cell GAD in a patient. Briefly, a sample of a biological fluid is obtained from a patient diagnosed as having non-insulin-dependent diabetes, and the sample is contacted with a human islet cell GAD polypeptide under conditions conducive to immune complex formation. The presence of immune complexes indicates the presence of autoantibodies to human islet cell GAD in the sample. Immune complexes are detected by such methods as enzyme reaction, fluorescence, luminescence or radioactivity. Thus, within one embodiment, the GAD polypeptide may be labeled, such as with a radionuclide, to provide for detection of immune complexes. Within another embodiment, the immune complex is detected using a second antibody, such as an antibody labeled with a radionuclide.

A third aspect of the present invention provides methods for predicting the clinical course of diabetes in a patient comprising testing a biological fluid from a patient diagnosed as having non-insulin-dependent diabetes for the presence of human islet cell GAD, and classifying the patient for clinical course of diabetes based on the quantity of GAD in the fluid.

These and other aspects of the invention will become evident upon reference to the following detailed description and the attached drawings.

DETAILED DESCRIPTION OF THE INVENTION

Figure 1:
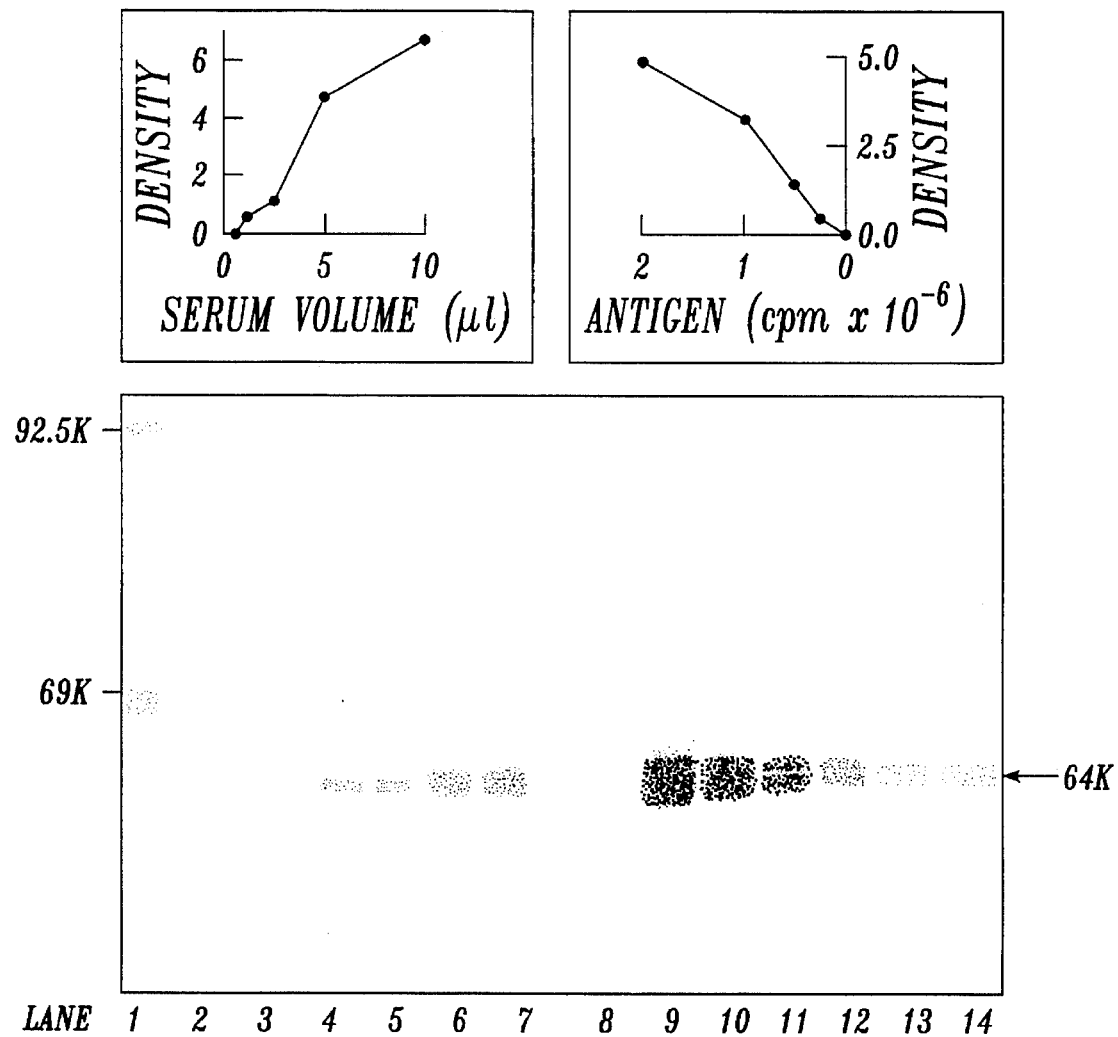
FIG. 1 shows the effect of antigen and antibody concentration on a GAD immunoprecipitation assay. (Left) Immunoprecipitations using 0.63, 1.25, 2.5, 5 and 10 μl of one GAD Ab-positive diabetic serum in lanes 3, 4, 5, 6 and 7, respectively. Lane 1, molecular weight markers. Lane 2, immunoprecipitation using normal human serum. (Inset) Densitometric scanning of lanes 2–7. Density is given in arbitrary units. (Right) Decreasing amounts of transfected BHK cell membrane detergent extract from 2, 1, 0.5 and 0.25×10⁶ cpm in lanes 9, 10, 11 and 12, respectively, were precipitated with 10 μl of strongly positive diabetic serum. Lane 14 uses 10 μl healthy control serum. Lane 13 shows reprecipitated supernatant from the lane 10 immunoprecipitation. (Inset) Densitometric scanning of lanes 9–13.

The present invention provides methods for predicting the clinical course of diabetes through the detection of autoantibodies against human islet cell GAD. Detection of such autoantibodies is facilitated by the availability of human islet cell GAD polypeptides made possible by molecular cloning.

The methods of the present invention appear to be superior to previously described diagnostic techniques for detecting IDDM in patients with apparent NIDDM. Experiments described herein show the GAD antibody assay to have a better predictive value than body mass index (BMI) or C-peptide levels. GAD antibody testing also appears to be as effective or nearly as effective as ICA testing. However, unlike the ICA test, the methods of the present invention do not require pancreatic tissue sections from the patient, and they avoid the inherent variability and technical difficulty of the ICA assay (Greenbaum et al., *Diabetologia* 35:798–800 (1992)).

Recombinant DNA expression systems provide convenient means for obtaining large quantities of recombinant human islet cell GAD and fragments thereof in relatively pure form for use in diagnostic assays. By "recombinant" is meant a polypeptide produced by a recombinant expression system and typically free of native endogenous substances. The term "polypeptide" is meant to include sequences of at least about six amino acids, typically 10 to 25, and up to 100–200 amino acids or more, including up to the entire human islet cell GAD protein, and containing at least one epitope recognized by GAD autoantibodies. Representative human islet cell GAD DNA and amino acid sequences are shown in SEQ ID NO: 1 and SEQ ID NO: 2. Those skilled in the art will recognize that allelic variations in these sequences will exist, and that additional equivalent sequences can be generated by genetic engineering. Such equivalent sequences will comprise minor sequence changes, including conservative amino acid substitutions. Substitutions may be designed based on, for example, the model of Dayhoff, et al. (in *Atlas of Protein Sequence and Structure* 1978, Nat'l Biomed. Res. Found., Washington, D.C.). DNA sequence modifications can result in changes in the amino acid sequence, provide silent mutations, modify a restriction site, or provide other specific mutations. The degeneracy of the genetic code allows considerable design flexibility when preparing DNA sequences encoding GAD.

Human islet cell GAD protein contains certain sequence domains that are variable, differing at least about 15%, more typically at least about 20%, from analogous regions of GADs of other tissues and/or species, while other regions of the human islet cell GAD are identical or nearly identical to other GADs and thus represent conserved regions. The conserved and variable sequence regions of human islet cell GAD can be determined by techniques known to the skilled artisan, such as sequence alignment techniques, e.g., using the Sequence Analysis Software Package of the Genetics Computer Group, University of Wisconsin Biotechnology Center, 1710 University Avenue, Madison, Wis. 53705 (Devereux, *Nuc. Acids. Res.* 12:387–396 (1984)). Homology is determined by attaining optimal alignment of the human islet cell GAD sequence with, e.g., brain GAD sequences of rat and cat, as disclosed in Julien et al., *J. Neurochem.* 54:703–705 (1990), incorporated herein by reference.

For example, in reference to SEQ. ID NO. 2, human islet GAD variable region domains, when compared to the amino acid sequence of cat and rat GAD, are identified at the N-terminal residues 1–91, and at positions 137–171, 405–431, and 511–540. Within assay systems using small GAD peptides to detect autoantibodies, epitopes which comprise at least a portion of a variable region domain, typically at least about six contiguous amino acids from the variable region and often ten or more residues, provide human islet cell GAD-specific markers.

Nucleic acid sequences encoding human islet cell GAD as described herein can be cloned directly from human cell sources that express the enzyme. Preferred sources include human pancreatic islet cells. Useful nucleic acid sequences for cloning and expressing GAD sequences include mRNA, genomic DNA and cDNA, although for expression cDNAs are generally preferred because they lack introns that may interfere with expression.

To obtain a human islet GAD clone, a cDNA library prepared from, e.g., human pancreatic islet cells is screened with labeled probes from the human islet GAD sequences provided herein, or from homologous sequence regions of, e.g., mouse brain GAD (Katarova et al., *Eur. J. Neurosci.* 2:190–202 (1990)), cat brain GAD (Kabayashi et al., *J Neurosci.* 7:2768–2772 (1987)), or rat brain GAD (Julien, et al., *J. Neurochem.* 54:703–705 (1990)), each of which is incorporated herein by reference. An oligo-dT primed cDNA library can be constructed with polyA⁺ RNA purified from human pancreatic islet cells or from other tissues/cells as desired. The library is screened with, e.g., antibodies to homologous GAD and/or labeled probes. Partial clones may be used as probes in additional screening until the complete coding sequence is obtained. If necessary, partial clones are joined in the correct reading frame to construct the complete coding sequence. Joining is achieved by digesting clones with appropriate restriction endonucleases and joining the fragments enzymatically in the proper orientation. Depending on the fragments and the particular restriction endonucleases chosen, it may be necessary to remove unwanted DNA sequences through a "loop out" process of deletion mutagenesis or through a combination of restriction endonuclease cleavage and mutagenesis. It is preferred that the resultant sequence be in the form of a continuous open reading frame, that is, that it lack intervening sequences (introns).

Representative human islet cell GAD cDNA clones isolated as described herein can be combined to give the full coding sequence for the human islet cell GAD. For example, two clones, designated pHIG1.9 and pHIG11, are combined to give the full coding sequence and 3'-untranslated sequences, SEQ ID. NO. 1. This clone has a polyadenylation sequence upstream of a poly A sequence at the 3' end. The identity of a human islet cell GAD clone can be confirmed by, for example, in vitro translation and subsequent immunoreactivity and migration on an SDS-polyacrylamide gel, sequencing, or by appropriate enzymatic activity, e.g., catalyzing the synthesis of γ-aminobutyric acid. GAD catalytic activity can be assayed by $CO_2$ and/or GABA methods as described in, e.g., Chude and Wu, *J. Neurochem.* 27:83–86 (1976). Briefly, the assays can employ, e.g., L-[U-$^{14}$C] glutamate as a substrate and the amounts of $^{14}CO_2$ and [$^{14}$C]GABA formed are determined.

For expression, a DNA sequence encoding human islet GAD is inserted into a suitable expression vector, which in turn is used to transform or transfect appropriate host cells for expression. Suitable host cells are those cell types that can be transformed or transfected with exogenous DNA and grown in culture, and include bacteria, fungal cells, and cultured higher eukaryotic cells. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y. (1989), which is incorporated herein by reference. Those skilled in the art will recognize that GAD can also be produced through in vitro transcription and translation.

In general, the DNA sequence encoding GAD is operably linked to a transcription promoter and terminator within an expression vector. The vector will commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct recombinant GAD into the secretory pathway of the host cells, a secretory signal sequence (also known as a leader sequence, prepro sequence or pre sequence) is provided in the expression vector. The secretory signal sequence is joined to the DNA sequence encoding the mature GAD protein or a fragment thereof in the correct reading frame. Secretory signal sequences are commonly positioned 5' to the DNA sequence encoding the protein of interest, although certain signal sequences may be positioned 3' to the DNA sequence of interest (see, e.g., Welch et al., U.S. Pat. No. 5,037,743; Holland et al., U.S. Pat. No. 5,143,830).

Cultured mammalian cells are preferred as hosts for expression of GAD. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841–845, 1982) and DEAE-dextran mediated transfection (Ausubel et al., eds., *Current Protocols in Molecular Biology*, John Wiley and Sons, Inc., New York, 1987). The production of recombinant proteins in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134, which are incorporated herein by reference. Preferred cultured mammalian cells include the COS-1 (ATCC No. CRL 1650), COS-7 (ATCC No. CRL 1651), BHK (ATCC No. CRL 1632), BHK 570 (ATCC No. CRL 10314) and 293 (ATCC No. CRL 1573; Graham et al., *J. Gen. Virol.* 36:59–72, 1977) cell lines. Additional suitable cell lines are known in the art and available from public depositories such as the American Type Culture Collection, Rockville, Md.

Other higher eukaryotic cells may also be used as hosts, including insect cells, plant cells and avian cells. Transformation of insect cells and production of foreign proteins therein is disclosed by Guarino et al., U.S. Pat. No. 5,162,222 and Bang et al., U.S. Pat. No. 4,775,624, which are incorporated herein by reference. The use of *Agrobacterium rhizogenes* as a vector for expressing genes in plant cells has been reviewed by Sinkar et al., *J. Biosci. (Bangalore)* 11:47–58 (1987).

Yeast cells, particularly cells of the genus Saccharomyces, are also suitable hosts for use within the present invention. Methods for transforming yeast cells with exogenous DNA and producing recombinant proteins therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075, which are incorporated herein by reference. A preferred vector system for use in yeast is the POT1 vector system disclosed by Kawasaki et al. (U.S. Pat. No. 4,931,373), which allows transformed cells to be selected by growth in glucose-containing media. Transformation systems for other yeasts, including *Hansenula polymorpha, Schizosaccharomyces pombe, Kluyveromyces lactis, Kluyveromyces fragilis, Ustilago maydis, Pichia pastoris, Pichia guillermondil* and *Candida maltosa* are known in the art. See, for example, Gleeson et al., *J. Gen. Microbiol.* 132:3459–3465 (1986) and Cregg, U.S. Pat. No. 4,882,279.

Other fungal cells are also suitable as host cells. For example, Aspergillus cells may be utilized according to the methods of McKnight et al., U.S. Pat. No. 4,935,349, which is incorporated herein by reference. Methods for transforming *Acremonium chrysogenum* are disclosed by Sumino et al., U.S. Pat. No. 5,162,228, which is incorporated herein by reference.

Preferred prokaryotic host cells for use in carrying out the present invention are strains of the bacteria *Escherichia coli*, although Bacillus and other genera are also useful. Techniques for transforming these hosts and expressing foreign DNA sequences cloned therein are well known in the art (see, e.g., Sambrook et al., ibid.).

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Recombinant GAD is conveniently prepared from host cells as a cell membrane fraction. Cells are disrupted by suspending them in 20 mM Tris-HCl, pH 7.4, 150 mM NaCl, 0.5 mM methionine, 10 mM benzamidine-HCl or a similar buffer supplemented with 1% aprotinin, 5 mM EDTA, 0.1 mM p-chloromercuribenzenesulfonic acid and 1% Triton X-114 (Sigma Chemical Co., St. Louis, Mo.) or a like detergent. After 2–4 hours on ice the solution is centrifuged, and the lysate supernatant (detergent extract) is recovered (Baekkeskov et al., *J. Clin. Invest.* 79:926–934 (1987)). Further separation of membrane fractions may be achieved using phase condensation techniques (Bordier, *J. Biol. Chem.* 256:1604–1607 (1981)). For preparation of antigen to be used in diagnostic assays, the GAD may be conveniently labeled by culturing the host cells in the presence of a label, such as $^{35}$S-methionine, $^{3}$H-leucine or $^{35}$S-cystine Recombinant human islet cell GAD may be further purified by affinity chromatography on an antibody column using antibodies, preferably monoclonal antibodies, directed against GAD. Additional purification may be achieved by conventional chemical purification means, such as liquid chromatography, gradient centrifugation, and gel electrophoresis, among others. Methods of protein purification are known in the art (see generally, Scopes, *Protein Purification*, Springer-Verlag, N.Y. (1982), which is incorporated herein by reference) and may be applied to the purification of the recombinant human islet cell GAD described herein. Substantially pure recombinant human islet cell GAD of at least about 50% is preferred, at least about 70–80% more preferred, and 95–99% or more homogeneity most preferred, particularly for pharmaceutical uses. Once purified, partially or to homogeneity, as desired, the recombinant human islet GAD is used diagnostically as further described herein below.

Human islet cell GAD polypeptides can also be produced by fragmenting larger purified recombinant GAD polypeptides with a protease or a chemical agent, or by producing recombinant polypeptide fragments. Synthetic islet cell GAD peptides can also be produced from the amino acid sequences provided herein, using conventional solid-phase synthesis procedures as described in, e.g., Merrifield, *Fed. Proc.* 21:412 (1962) and Barany and Merrifield, in *The Peptides*, Vol. 2, pp. 1–284 (1979) Academic Press, New York, which are incorporated herein by reference. Short polypeptide sequences, or libraries of overlapping peptides, usually from about 6 up to about 35 amino acids, which correspond to selected human islet cell GAD regions, can be readily synthesized and then screened in screening assays designed to identify peptides that represent immunodominant epitopes (particularly those recognized by autoantibodies). Recombinant polypeptides can be produced by expressing GAD DNA fragments, such as fragments generated by digesting a human islet cell GAD cDNA at convenient restriction sites. The isolated recombinant polypeptides or cell-conditioned media are then assayed for the presence of epitopes as described above.

Although the use of recombinant GAD is preferred within the methods of the present invention, GAD may also be prepared from cells that naturally produce it (such as human islet cells). For example, GAD may be prepared from human islets by isolation of a membrane fraction. This GAD-enriched fraction is then used to detect GAD autoantibodies.

Human islet cell GAD polypeptides produced as described above are used diagnostically in the detection and quantification of anti-GAD autoantibodies or the detection of free GAD (as a measure of beta cell destruction) in a biological sample, that is, any sample derived from or containing cells, cell components or cell products, including, but not limited to, cell culture supernatants, cell lysates, cleared cell lysates, cell extracts, tissue extracts, blood, plasma, serum, urine, and fractions thereof. By means of having human islet cell GAD polypeptides which specifically bind to human islet cell GAD autoantibodies, the concentration of the autoantibodies in an individual can be measured, which level can then be used to monitor the progression or regression of the potentially harmful autoantibodies in individuals at risk. The inventors have found that these assays can be used to predict the development of IDDM in apparent NIDDM patients.

As will be recognized by those skilled in the art, numerous types of immunoassays are available for use in the present invention. For instance, direct and indirect binding assays, competitive assays, sandwich assays, and the like are generally described in, e.g., U.S. Pat. Nos. 4,642,285; 4,376,110; 4,016,043; 3,879,262; 3,852,157; 3,850,752; 3,839,153; 3,791,932; and Harlow and Lane, *Antibodies, A Laboratory Manual*, Cold Spring Harbor Publications, New York (1988), each incorporated by reference herein. In one assay format anti-human islet cell GAD autoantibodies in a biological sample are quantified directly by measuring the binding of antibodies to recombinant or synthetic GAD polypeptides. The biological sample is contacted with at least one human islet cell GAD polypeptide under conditions conducive to immune complex formation. The immune complexes formed between the GAD polypeptide and the antibodies are then detected, and the presence of the autoantibodies to human islet cell GAD in the sample is determined. The immune complexes can be detected by means of, e.g., labeled antibodies, such as anti-IgG, IgM and/or IgA human antibodies, or antibodies which bind to the human GAD. Separation steps (e.g., washes) may be necessary in some cases to distinguish specific binding over background. In another format, a patient's antibodies or serum GAD can be measured by competing with labeled or unlabeled antibodies to GAD or GAD polypeptides, respectively, for binding. Unlabeled GAD may be used in combination with labeled antibodies which bind to human antibodies or to GAD. Alternatively, the GAD polypeptide may be directly labeled. A wide variety of labels may be employed, such as radionuclides, particles (e.g., gold, ferritin, magnetic particles, red blood cells), fluors, enzymes, enzyme substrates, enzyme cofactors, enzyme inhibitors, ligands (particularly haptens), chemiluminescers, biotin and other compounds that provide for the detection of the labeled polypeptide or protein. For example, highly purified GAD or GAD polypeptide may be radiolabeled using conventional methods of chemical substitution on polypeptide tyrosine residues with $^{125}$I of high specific activity. In this format, radiolabeled GAD is combined with patient serum under conditions suitable for immune complex formation. Immune complexes are then separated, such as by binding to protein A. Precipitated GAD is then quantitated by conventional methods, such as gel electrophoresis, fluorography, densitometry or by direct counting of immunoprecipitated, radiolabeled antigen. The amount of GAD precipitated by test sera is then statistically compared to mean counts precipitated by a large number (preferably >50) of healthy human control sera, each measured separately. In an alternative format, the GAD antigen, labeled with biotin, is combined with patient serum under conditions suitable for immune complex formation. The serum is then transferred to a protein A-coated container, such as a well of an assay plate, and the container is allowed to stand so that immune complexes can form. The container is then washed, and streptavidin, conjugated to a suitable enzyme (e.g. alkaline phosphatase), is added. A chromogenic substrate is then added, and the presence of GAD autoantibodies in the sample is indicated by a color change. Additional assay formats will be evident to those skilled in the art.

Thus, autoantibodies to β-islet cell GAD autoantigens may be identified and, if desired, extracted from patient's serum by binding to the GAD. The GAD polypeptide may be attached, e.g., by adsorption, to an insoluble or solid support, such as an ELISA microtiter well, microbeads, filter membrane, insoluble or precipitable soluble polymer, etc. to function as an affinity resin. The captured autoantibodies may then be identified by several methods. For example, antisera or monoclonal antibodies may be used. These antisera or monoclonal antibodies are typically non-human in origin, such as rabbit, goat, mouse, etc. These antiantibodies may be detected directly if attached to a label such as $^{125}I$, an enzyme, biotin, etc., or may be detected indirectly by a labeled secondary antibody made to specifically detect the anti-antibody.

Kits can also be supplied for use with the recombinant or synthetic human islet GAD polypeptides in detecting autoantibodies to pancreatic β-islet cells. Thus, GAD polypeptides may be provided, usually in lyophilized form, in a container, either alone or in conjunction with additional reagents, such as GAD-specific antibodies, labels, and/or anti-human antibodies and the like. The GAD polypeptide and antibodies, which may be conjugated to a label or unconjugated, are included in the kits with buffers, such as Tris, phosphate, carbonate, etc., stabilizers, biocides, inert proteins, e.g., serum albumin, or the like. Frequently it will be desirable to include an inert extender or excipient to dilute the active ingredients, where the excipient may be present in from about 1 to 99% of the total composition. Where an antibody capable of binding to the islet cell GAD autoantibody or to the recombinant or synthetic GAD is employed in an assay, this will typically be present in a separate vial.

Although the diagnostic methods of the present invention are highly predictive for IDDM, they may be used in conjunction with other known assays and diagnostic techniques. Such other assays and techniques include measurement of body mass index (BMI), defined as the quotient of the patient's weight in kg divided by the square of height in meters; C-peptide level (Heding, *Diabetologia* 11: 541–548 (1975); Landin-Olsson et al., *Diabetologia* 33: 561–568 (1990)); or one or more additional diabetes-specific autoantibodies. Other diabetes-specific autoantibodies include antibodies to insulin (Palmer et al., *Science* 222:1337–1339 (1983); Nakanishi et al., *Diabetes Res.* 9:105–109 (1988)), carboxypeptidase H (Castano et al., *J. Clin. Endocrinol. and Metab.* 73:1197–1201 (1991)), p69 β-cell surface protein (Karjalainen et al., *N. Engl. J. Med.* 327: 302–307 (1992)), sulfatide (Buschard et al., *APMIS* 99(12): 1151–1156 (1991)), 37 kDa tryptic fragment (Christie et al., *J. Exp. Med.* 172: 789–794 (1990)), 38 kDa β-cell component (Baekkeskov et al., *Nature* 298: 167–169 (1982)) and p52 antigen (Karounos et al., *Diabetes* 39: 1085–1090 (1990)). See also review by Harrison (*Immunol. Today* 13(9):348–352 (1992)). The presence of autoantibodies to these and other antigens can be determined by methods known in the art. Of particular interest are BMI and C-peptide level. A low BMI (i.e. less than about 25) in combination with other indicators is suggestive of type I diabetes. BMI is thus a useful indicator for distinguishing type I from type II diabetes. C-peptide level can be measured using standard methods, such as that of Heding (ibid.), in which insulin and proinsulin are removed from serum and C-peptide is measured in the resulting insulin-free fraction radioimmunologically.

Antibodies for diagnostic or therapeutic uses which bind human islet cell GAD and/or islet cell GAD polypeptides can be produced by a variety of means. The production of non-human monoclonal antibodies, e.g., murine antibodies, is well known and may be accomplished by, for example, immunizing the animal with a recombinant or synthetic GAD molecule or a selected portion thereof (e.g., a peptide). For example, by selected screening one can identify a region of the GAD molecule such as that predominantly responsible for recognition by anti-GAD autoantibodies, or a portion which comprises an epitope of an islet cell GAD variable region, which may thus serve as an islet cell GAD-specific marker. Antibody producing cells obtained from the immunized animals are immortalized and screened, or screened first for, e.g., the production of antibody which inhibits the interaction of the anti-GAD autoantibody with the GAD molecule and then immortalized. As the generation of human monoclonal antibodies to a human antigen, such as the human islet cell GAD molecule, may be difficult with conventional immortalization techniques, it may be desirable to first make non-human antibodies and then transfer via recombinant DNA techniques the antigen binding regions of the non-human antibodies, e.g. the $F(ab')_2$ or hypervariable regions, to human constant regions (Fc) or framework regions to produce substantially human molecules. Such methods are generally known in the art and are described in, for example, U.S. Pat. No. 4,816,397 and EP publications 173,494 and 239,400, which are incorporated herein by reference. Alternatively, one may isolate DNA sequences which encode a human monoclonal antibody or portions thereof that specifically bind to the human islet cell GAD protein by screening a DNA library from human B cells according to the general protocol outlined by Huse et al., *Science* 246:1275–1281 (1989), incorporated herein by reference, and then cloning and amplifying the sequences which encode the antibody (or binding fragment) of the desired specificity.

The following examples are offered by way of illustration, not limitation.

EXAMPLE I

Cloning and Sequencing of Human Islet Cell GAD

Islet cells were isolated from human pancreata obtained from organ transplant donors for whom a matched recipient was not available. After in situ perfusion with cold UW solution (Du Pont, Boston, Mass.), each pancreas was carefully excised, the pancreatic duct cannulated, and 4 mg/ml collagenase solution (Type V, Sigma, St. Louis, Mo.) infused at a constant rate, first at 4° C. and then 39° C. The gland was teased apart, and liberated fragments were washed by centrifugation, triturated through needles of decreasing caliber, and purified by discontinuous Ficoll density centrifugation (G. L. Warnock, *Diabetes* 35: Suppl. 1, pp. 136–139, January 1989). Material harvested from the upper interfaces was pooled and counted after a determination of islet purity by dithiazone staining. Islets used in library construction were greater than 65% pure, while islets used in Northern blots were greater than 40% pure. The average islet diameter was 175 μm. Additionally, the isolated islets showed both first and second phase insulin secretory function after perfusion with either high glucose or with isobutylmethylxanthine (IBMX).

Poly(A)+ RNA was isolated using a FastTrack™ mRNA isolation kit (Invitrogen, San Diego, Calif.) according to the manufacturer's instructions. Briefly, 30,000 purified islets were quickly lysed in lysis buffer, homogenized using needles of decreasing caliber, and digested in the presence of proteinase K and RNasin, then poly(A)+ RNA was selected by oligo-d(T) cellulose chromatography. The concentration and purity of the eluted fractions were determined at $OD_{260/280}$.

Approximately 2.5 µg poly(A)+ RNA from the human islets was used for cDNA library construction using a Librarian R II cDNA library construction system (Invitrogen) and Electromax™ DH10B *E. coli* cells (GIBCO BRL, Gaithersburg, Md.) according to the manufacturer's instructions. In short, approximately 2.5 µg of poly(A)+ RNA, isolated from human islets, was converted into double-stranded cDNA, followed by the addition of BstX I nonpalindromic linkers (Invitrogen). The cDNA was size fractionated, and the unreacted linkers were removed by agarose gel electrophoresis and electroelution. Complementary DNA strands larger than 600 bp were selected and ligated into the Librarian R II pcDNA II vector. Following electroporation of a fraction of the ligated material into DH10B *E. coli* cells, a total of 2×10⁶ colonies with a background of approximately 10% was screened by hybridization. These colonies were replicated in duplicate to nylon filters, lysed, neutralized, washed and baked essentially as described by Sambrook et al., *Molecular Cloning, A Laboratory Manual*, Cold Spring Harbor Press, Cold Spring Harbor, N.Y. (1989), incorporated herein by reference.

To identify colonies containing human islet GAD cDNA, 20-mer oligonucleotide probes representing conserved regions from three different homologous nucleotide sequences of the internal as well as the N- and C-terminal parts of the coding regions of cat (Kobayashi et al., *J. Neurosci.* 7:2768–2772 (1987)), rat (Julien et al., *J. Neurochem.* 54:703–705 (1990)), and mouse (Katarova et al., ibid.) brain GAD were synthesized (Table 1), $^{32}$P-ATP labeled by kinasing and used to screen the nylon filter replicas of the human islet cDNA library. Following hybridization and consecutive washings at increasing stringency, six positive colonies representing insert sizes from 0.7 to 1.4 kb were selected for colony purification and subsequent sequence analysis. By rescreening the library with a 600 bp PvuII-PstI fragment of a circa 1300 bp clone containing 1281 base pairs of the 3' coding sequence (pHIG1.3), another clone, pHIG1.9, FIG. 1, with a 1.9 kb insert, was isolated.

with primers bybridizing to the flanking SP6 and T7 promoters. As the sequencing progressed, new primers representing 20-mer 3' oligonucleotides of the insert were synthesized and used to obtain the entire sequence of the human islet GAD cDNA inserts. The nucleotide sequences were analyzed with the sequence analysis software package of the University of Wisconsin genetics computer group (Devereux, *Nuc. Acids. Res.* 12:387–396, (1984), incorporated herein by reference).

To obtain full-length clones, the 5' cDNA ends of two clones were extended using a variation of the PCR-RACE protocol (Frohman et al., *Proc Natl. Acad. Sci. USA* 85:8998–9002, (1988)). Oligonucleotide primers (ZC3614, ZC3623, Table 2) complementary to a region near the 5' end of GAD clones, and containing adapter sequences with an Eco RI restriction site, were annealed with an aliquot of islet cell poly(A)+ RNA. Following extension, the products were terminal deoxynucleotidyltransferase-tailed with dGTP, and a poly-dCTP primer with an Eco RI adapter (ZC2488, Table 2) was used on second strand synthesis to generate a cDNA population enriched for GAD but still heterogeneous due to non-specific pairing of the internal primer. As a second step, a second oligonucleotide complementary to a region upstream from the internal primer (ZC3746 upstream of ZC3614, or ZC3745 upstream of ZC3623; Table 2), was used to prime the minus strand while a primer complementary to the Eco RI adapter (ZC2633; Table 2) was used to prime the plus strand. PCR amplification yielded further enrichment of GAD sequences. Using the GeneAmp PCR kit (Perkin-Elmer Cetus, Norwalk, Conn.), the reaction was cycled 40 times at 94° C. for 1 minute to denature, 50° C. for two minutes and 72° C. for 2 minutes. The resulting products were electrophoresed on an agarose gel, and the GAD sequences were eluted, digested with Eco RI and cloned into the vector pUC19.

TABLE 1

SEQ ID NO: 3 5'-GCGGGAGCGGATCCTAATACTACCAACCTGCG-3' ZC3338 5' probe
SEQ ID NO: 4 5'-ACCATGGTTGTTCCTGACTCCATCAT-3' ZC3339 3' probe
SEQ ID NO: 5 5'-CTGACATCAACTGCCAATACCAATATGTTCACATATG-AAATTGCA-3'
ZC3337 main probe, primary screen For DNA sequencing, plasmids were isolated from positive clones by the rapid boiling method (Homes and Quigley, *Anal. Biochem.* 114:193–197 (1981)). The resulting double-stranded cDNA was sequenced using the Sequenase® kit (version 2.0, United States Biochemical, Cleveland, Ohio)

TABLE 2

| | |
|---|---|
| SEQ ID NO: 6 | 5'-AAATGAGAATTCACACGCCGGCAGCAGGTC-3' ZC3614 |
| SEQ ID NO: 7 | 5'-AAGGAATTCAAGTTGATTGAAGTATCT-3' ZC3623 |
| SEQ ID NO: 8 | 5'-GGCGAATTCGCATATTTTAGAGTTGTTTGG-3' ZC3745 |
| SEQ ID NO: 9 | 5'-GGCGAATTCGGAGCAGCTGCAGGGCTTCTG-3' ZC3746 |
| SEQ ID NO: 10 ZC2633 | 5'-AGGGAGACCGGAATTCGACTCGAGTCGACATCGATCAG-3' |
| SEQ ID NO: 11 ZC2488 | 5'-GACTCGAGTCGACATCGATCAGCCCCCCCCCC-3' |

Double-stranded plasmids containing the 5' end of the GAD sequence inserted into pUC19 were sequenced in the same manner as the positive clones initially isolated from the library using the primers in Table 3.

TABLE 3

SEQ ID NO: 12 5'-GGCGATTAAGTTGGGTAA-3'
SEQ ID NO: 13 5'-TAACAATTTCACACAGG-3'

The entire sequence of the human islet cell GAD cDNA is shown in SEQ. ID. NO. 1. It was determined by assembling a composite of two overlapping cDNA clones, pHIG 11 and pHIG1.9, and of five RACE reaction products, RACE 20, 28A, 47A, 41 and 42. The two cDNA clones overlap by 110 bp, and the five RACE sequences were designed to overlap with pHIG 1.9 by 140 nucleotides at the 3' end. The pHIG 1.9 clone comprises 1900 bp and encodes the pyridoxal 5'-phosphate binding site (Pro-His-Lys-Met-Met-Gly, SEQ ID NO: 17) at amino acids 394–399, a stop codon following the C-terminal Leu codon and a polyadenylation site (AAATAAA), 17 nucleotides upstream of a poly A sequence at the 3' end (SEQ ID NO: 1). pHIG 11 extended the 5' end of the cDNA sequence to 250 bp upstream from the predicted N-terminal Met. pHIG1.1 contains an intron as a cloning artifact from an aberrantly spliced RNA.

The human islet cell GAD cDNA nucleotide sequence had a overall homology of only about 70% to the brain GAD cDNA sequences of the rat, cat and mouse, whereas the brain sequences showed about 91% homology among the three. The predicted amino acid sequence homology between the human islet cell GAD and those of the brain sequences of cat, rat and mouse is about 76% again in contrast to the more than about 98% homology found among the brain GAD amino acid sequences. Comparison of the 5' end of the human islet sequence to the 68 amino acid 5' end of the human testis GAD (Perrson et al., *Mol. Cell. Biol.* 10:4701–4711 (1990)) shows differences at 15 amino acid positions, whereas only two amino acid substitutions have been found between the human testis sequence and rat brain GAD.

EXAMPLE II

Expression of GAD cDNA

Expression of the human islet GAD cDNA (SEQ ID NO: 1) required that the two overlapping clones, pHIG11 and pHIG1.9 be assembled into a single, full-length clone. The 5' sequence from the open reading frame of clone pHIG11 was isolated using a polymerase chain reaction. Oligonucleotides were synthesized so the 5' end of one primer was positioned at the ATG initiation codon and contained the following sequence:

5' CCA GTC TGA ATT CAC CAT GCT AGC CCA GGC TCC GGA T 3' (SEQ ID NO: 14)

The 3' oligonucleotide primer began at a NsiI site, 482 nucleotides downstream of the initiation codon, and contained the following sequence:

5' TTT TAG AGA AGC TTG GCA ATG CAT CAA AAT TTC CTC C 3' (SEQ ID NO: 15).

A 0.5 kb DNA fragment was isolated by digestion at the EcoRI (5') and HindIII (3') restriction sites, and after sequence analysis was found to be the correct size. The EcoRI site was altered to a BamHI site using the synthetic oligonucleotide 5' ATT GGA TCC 3'. The resulting 0.5 kb DNA fragment was then isolated using the BamHI (5') and the NsiI (3') restriction sites.

The remaining DNA sequence of the GAD cDNA was isolated as 2 cDNA fragments from the clone designated pHIG1.9. The internal DNA fragment was isolated using the restriction enzymes NsiI (5') and BglII (3'). The resulting fragment was found to be 0.6 kb. The 3' end of the GAD cDNA sequence was isolated by digestion of the clone pHIG1.9 with the restriction enzymes BglII (5') and XbaI (3'), and the resulting fragment was found to be 0.72 kb.

The expression plasmid was made from a four-part ligation reaction that included the 5' BamHI-NsiI fragment, the internal NsiI-BglII fragment, the 3' BglII-XbaI fragment and the expression vector Zem 219b.

The vector Zem 219b was constructed in the following manner. Plasmid pIC19R (Marsh et al., *Gene* 32:481–486 (1984)) was digested with SmaI and Hind III. The ori region of SV40 from map position 270 (PvuII) to position 5171 (HindIII) was then ligated to the linearized pIC19R to produce plasmid Zem67. This plasmid was then cleaved with BglII, and the terminator region from the human growth hormone gene (De Noto et al., *Nuc. Acids Res.* 9: 3719–3730 (1980)) was inserted as a BglII-BamHI fragment to produce plasmid Zem86. A synthesized human plasminogen activator (t-PA) pre-pro sequence in pUC8 was isolated by digestion with BamHI and XhoII. This fragment was inserted into BglII-digested Zem86 to produce plasmid Zem88. Plasmid pDR1296 (ATCC 53347) was digested with BglII and BamHI, and the t-PA cDNA fragment was isolated and inserted into BglII-cut Zem88. The resultant plasmid was designated Zem94. The vector Zem99, comprising the MT-1 promoter, complete t-PA coding sequence, and the human growth hormone (hGH) terminator, was then assembled. A KpnI-BamHI fragment comprising the MT-1 promoter was isolated from MThGH111 (Palmiter et al., *Science* 222:809–814 (1983)) and inserted into pUC18 to construct Zem93. Plasmid EV142, comprising MT-1 and hGH sequences in the pBR322 derivative pBX322 (Palmiter et al., ibid.), was digested with EcoRI, and the fragment comprising the MT-1 promoter and hGH terminator sequences was isolated. This fragment was cloned into EcoRI-digested pUC13 to construct plasmid Zem4. Zem93 was then linearized by digestion with BglII and SalI, and the hGH terminator was purified. The t-PA pre-pro sequence was removed from the pUC8 vector as a Sau 3A fragment. The three DNA fragments were then joined to produce plasmid Zem97. Zem97 was cut with BglII and the BglII-BamHI t-PA fragment from pDR1296 was inserted. The resultant vector was designated Zem99. Plasmid pSV2-DHFR (Subramani et al., *Mol. Cell Biol.* 1:854–864 (1981)) was digested with CfoI, and the fragment containing the DHFR cDNA and the 3' attached SV40 sequences was isolated, repaired, and ligated to BamHI linkers. After digestion with BamHI, an approximately 800 bp fragment containing the entire cDNA and the SV40 terminator region was purified and ligated to BamHI-digested pUCS. Zem67 was digested with BglII and ligated with the BamHI DHFR-SV40 fragment to generate plasmid Zem176. Plasmid Zem93 was digested with SstI and re-ligated to generate plasmid Zem106, in which approximately 600 bp of the sequence 5' to the MT-1 promoter was eliminated. Plasmid Zem106 was digested with EcoRI and ligated to the EcoRI fragment containing the DHFR gene from plasmid Zem176. The resulting plasmid was designated Zts14. Plasmid Zts14 was digested with BamHI and ligated to the BamHI fragment from plasmid Zem99 containing the entire t-PA coding region and hGH terminator sequence. The resulting plasmid was designated Zts15. Zts15 was partially digested with BamHI, repaired and re-ligated to generate plasmid Zem219, in which the 3' BamHI site was destroyed. Plasmid Zem219 was partially digested with XbaI, repaired and re-ligated to generate plasmid Zem219a, in which the XbaI site 3' to the hGH terminator was destroyed. Zem219b was derived from Zem219a by digesting that vector with BamHI and XbaI, removing the t-PA sequences, and ligating the vector fragment with a BamHI-XbaI adaptor. Zem219b has been deposited with American Type Culture Collection, Rockville, Md. as an *E. coli* XL1-blue transformant under accession no. 68979.

Expression of the GAD cDNA was achieved by transfection of the tk⁻ts13 BHK cell line (ATCC CRL 1632) using the calcium phosphate method (Graham and Van der Eb, ibid.). Transfectants were selected using a medium containing 400 nM methotrexate. The transfectants were tested for production of human GAD protein using immunocytochemistry. For testing immunoreactivity, two antibodies were used (Michelsen et al., *Proc. Natl. Acad. Sci. USA* 88:8754–8758 (1991)). The first antibody, designated 1266, was raised in rabbits immunized with the synthetic C-terminal sequence:

Thr-Gln-Ser-Asp-Ile-Asp-Phe-Leu-Ile-Glu-Glu-Ile-Glu-Arg-Leu-Gly-Gln-Asp-Leu(SEQ ID NO: 16)

The second antibody used for immunofluorescence labeling was raised against GABA (Immunotech, Marseille, France). The two-color double immunofluorescence labeling was carried out on fixed (1% paraformaldehyde, neutral) monolayers of transfected BHK cells to test the co-localization of the immunoreactivities of the C-terminal antiserum 1266 and antiserum against GABA. Texas Red-goat anti-rabbit IgG (1:100 dilution; Axell, Westbury, N.Y.) was used to detect primary antibodies. These assays showed that BHK cells transfected with human GAD cDNA expressed immunoreactive material while host cells without the GAD cDNA did not demonstrate reactivity.

A cell line (designated BHK K77.3) was chosen from the transfectants for its ability to stably produce intracellular human islet GAD. The recombinant GAD protein was purified from confluent cultures of $9.5 \times 10^8$ cells. The cells were pelleted by centrifugation at 350×g at room temperature for 4 minutes. The resulting cell pellet was homogenized in 20 ml of 50 mM sodium phosphate, 1 mM pyridoxal 5'phosphate (PLP), 1 mM amino-ethyl-isothiouronium-bromide (AET), 1 mM EDTA, 0.05% w/v aprotinin, 1% w/v Triton X-114 (TX-114) pH 8.0 (buffer A) and shaken gently for 1 hour at 4° C. for 30 minutes. Once in suspension the mixture was centrifuged at 100,000×g at 4° C. for 30 minutes. Twenty milliliters of supernatant was poured on top of 20 ml of 6% (w/v) sucrose, and the mixture was heated to 30° C. for 3 minutes. Following incubation the mixture was centrifuged at 3290×g for 5 minutes. The aqueous phase was extracted as described previously by adding 0.5% w/v TX-114 and applied to the same sucrose fraction as used previously. Nine ml of buffer A without TX-114 was added to the 1 ml detergent phase. The diluted TX-114 detergent phase of 10 ml was applied to a 1.0×1.6 cm GAD-1-Sepharose affinity column. GAD-1 is a monoclonal antibody against the human GAD protein. The column was washed in 40 ml of buffer A. The sample was applied to the column a total of three times. After the final application the column was washed with 70 ml of 50 mM sodium phosphate, 1 mM PLP, 1 mM AET, 0.05% aprotinin and 1% w/v n-octyl glucoside pH 8.0 (buffer B). The GAD was eluted with 50 mM $NH_4HCO_3$, 1% w/v n-octyl glucoside, 1 mM PLP and 1 mM AET pH 9.5 and collected in 500 µl fractions. Five hundred microliters of 50 mM sodium phosphate pH 7.0 was added to each fraction. The column was washed in buffer B and stored in PBS and 0.02% $NaN_3$. Ten microliter aliquots of the first ten fractions were analyzed using 1D-SDS polyacrylamide gel electrophoresis. Using a polyclonal antibody raised against the C-terminus of the human GAD protein, western analysis was done. In addition, the gel was stained with Coomassie brilliant blue, and enzymatic activity was measured as described in Wu (*Methods in Enzymology* 113:3–10 (1985)). Pools 4–14 were combined, and the total protein yield was calculated to be 27 µg or 27 ng/$10^6$ BHK cells. The protein purity was evaluated using a 2D-PAGE analysis, which showed a major spot at 64 kD, pI 6.4–6.7.

EXAMPLE III

Detection of GAD Autoantibodies

The GAD cDNA was inserted into the vector pcDNAII (Invitrogen, San Diego, Calif.) to construct pEx9 and transcribed in vitro. A reaction mixture was prepared by combining 20 µl of 5× SP6 transcription buffer (GIBCO BRL); 10 µl of 100 mM DTT; 100 units RNAsin; 7.5 µl of 2.5 mM each ATP, CTP and UTP; 2.5 μl of 1 mM GTP; 5 μl of 5 mM m7GpppG (cap analog); 2 μg linearized pEx9 DNA; 2 μl SP6 polymerase (GIBCO BRL) and distilled water to a final volume of 100 μl. The reaction mixture was incubated for 90 minutes at 37° C. The mixture was phenol-chloroform-isoamylalcohol extracted and then ethanol precipitated. The RNA pellet was resuspended in distilled water to a final concentration of 1 mg/ml.

The resulting synthetic mRNA was subjected to in vitro translation with $^{35}$S-methionine in a rabbit reticulocyte lysate system. The in vitro translation (IVT) reaction mixture contained 35 μl nuclease-treated rabbit reticulocyte lysate (Promega, Madison, Wis.), 50 units RNAsin, 1 μl amino acid mix (–Met), 1 μl $^{35}$S-methionine at a concentration of 150 Ci/mmol and 50 mCi/ml, and distilled water to a volume of 48 μl. The SP6 RNA, prepared as described above, was denatured at 67° C. for 10 minutes and then placed on ice. One microgram of the denatured SP6 RNA in a final volume of 2 μl was added to the IVT reaction mixture. The reaction mixture was incubated at 30° C. for 90 minutes. Two microliters of the reaction was precipitated with TCA to calculate percent incorporation as described by Sambrook et al. (ibid). The in vitro synthesized product represented a single Mr 64,000 protein.

The labeled, synthesized protein was used to screen sera for the presence of GAD autoantibodies. Protein A-Sepharose immunoprecipitation showed that sera from ten newly diagnosed IDDM children precipitated 11.6±2.9% (mean ±SEM) of the total radioactivity, compared with 2.3±0.5% in 22 healthy controls (p<0.001). Gel electrophoresis and autoradiography revealed that healthy controls remained negative while 8/10 IDDM sera precipitated the in vitro-synthesized protein. The specific immunoprecipitation with IDDM sera indicates that the major autoepitope is likely present on the nascent polypeptide and does not require post-translational modifications by an intact cell.

In a similar experiment, in vitro-synthesized, $^{35}$S-methionine-labeled GAD was used in an overnight radioligand binding assay using protein A-Sepharose to separate bound from free ligand. IMP buffer was prepared using 150 mM NaCl, 20 mM Tris pH 7.4, 1% Triton X-100, 0.1% Aprotinin, and 10 mM Benzamidine. A high salt IMP buffer was prepared with 400 mM NaCl substituted for the 150 mM NaCl. Forty-seven and one-half microliters of IMP buffer was added to 0.5 μl in vitro translated GAD and 2 μl of sera. The mixture was incubated by rotating overnight at 4° C. The Protein A-Sepharose was prewashed with IMP buffer and aliquoted into tubes at 50 μl/tube. The tubes were rotated for 1 hour at 4° C. The Protein A-Sepharose was then washed three times with 400 μl IMP buffer, one time with 400 μl high salt IMP buffer and one time with 400 μl IMP buffer. One hundred microliters of 1× SDS sample buffer, without any dyes, was added to each tube, and the mixture was boiled for 10 minutes. The supernatants were removed, added to 4 ml of scintillation fluid and counted. GAD antibody-positive (Juvenile Diabetes Foundation serum for ICA standardization) and negative control sera were included in each assay to express autoantibody levels as a 64K index. A 64K index is defined as:

mean cpm (sample)–mean cpm (negative control) mean cpm (positive control)–mean cpm (negative control)

The intra-assay coefficient of variation for duplicate determinations was 10.5%. In 38 0–15 year old controls the 64K index was –0.031±0.007 (mean ±SEM). In 62 new onset, 0–15 year old IDDM patients, the 64K index was 0.48±0.082. At a dilution of 1:25, the IDDM sera precipitated 11.7±1.6% of the total ligand radioactivity compared to 1.9±0.1% in the controls (p<0.001). Using a 64K index of 0.03 as the upper level of normal, no control (0/38) was positive compared to 48/62 (77%) of the IDDM patients. The 64K index in IDDM correlated to levels of ICA ($r_s$= 0.58; p<0.001). Thus, autoantibodies against synthetic human islet GAD can be accurately detected in a radioligand assay and are closely associated with newly diagnosed IDDM in children.

EXAMPLE IV

Detection of GAD Autoantibodies in NIDDM Patients

One hundred twenty patients (age range 6–79 yr., mean 37.9 yr.) were selected from 244 new-onset diabetics. The groups were defined by treatment with insulin (ins) or oral hypoglycemic agent/diet (OHA) at 0 and 18 months after onset as follows: group 1, ins/ins (n=37); group 2, OHA/OHA (n=62); group 3, OHA/ins (n=16); group 4, ins/OHA (n=5). Group 5 consisted of 33 normal healthy controls. Blood was sampled after an overnight fast as soon as possible, but always within three months of diagnosis and six months of first symptomatic hyperglycemia. Patients were characterized by age, family history, body mass index (BMI), and fasting C-peptide. Therapy at one week after diagnosis was defined as initial therapy, and therapy at 18 months follow-up and subsequently (range 18–49 months) was obtained from patient records. In a subset of 48 patients, further samples were drawn 1–2 yr. and 2–3 yr. later (66 total samples; not every patient was sampled at every time point).

Human islets were isolated, using collagenase digestion and Ficoll density gradient purification, from pancreata obtained with proper consent but for which a matched recipient was not found. Cells were labeled for 12 hours with $^{35}$S-methionine (Amersham Corp., Arlington Heights, Ill.) according to conventional procedures.

BHK K77.3 fibroblasts were biosynthetically labeled with $^{35}$S-methionine. Cells were grown for 10 hours at 30° C. in methionine-free medium supplemented to contain 2.5 mCi of $^{35}$S-methionine per 150 cm$^2$ flask of confluent cells.

For GAD isolation, radiolabeled cells were homogenized, and the membrane portion was isolated. Membranes were extracted with the detergent Triton X-114. After detergent phase condensation (Bordier, *J. Biol. Chem.* 256: 1604–1607, 1981), the membrane detergent phases of radiolabeled human islets and of radiolabeled BHK K77.3 fibroblasts were separately preincubated at 4° C. for 12 hours with normal human serum not subsequently used in the assay. Immunoglobulin was cleared using excess protein A-Sepharose (PAS; Zymed Laboratories Inc., South San Francisco, Calif.), and preclearing was repeated. The final supernatant was diluted in 10 mM Hepes buffer containing 0.25% (w/v) BSA, 0.1% (w/v) aprotinin (Novo Nordisk, Bagsvaerd, Denmark), 0.1 mM phenyl methyl sulfonyl fluoride (Sigma Chemical Co., St. Louis, Mo.), and 150 mM NaCl, at pH 7.4.

For each unknown serum assay, $\sim 5 \times 10^5$ cpm of BHK-derived antigen mixture in 590 µl was separately incubated with 10 µl of human serum for 12–16 hours at 4° C. with mixing. Immune complexes were precipitated with 80 µl of 1:2 PAS, washed at 4° C. four times in 10 mM Hepes, 0.25% Triton X-114, 150 mM NaCl, pH 7.5 and once with distilled $H_2O$, eluted into 2X Laemmli buffer/5% β-mercaptoethanol (βME; Eastman Kodak Co., Rochester, N.Y.), and analyzed by electrophoresis on 7.5% polyacrylamide gels containing sodium dodecyl sulfate (SDS-PAGE). Gels were treated with Entensify™ (New England Nuclear, Boston, Mass.) before fluorography. Parallel immunoprecipitations with monoclonal antibodies using human islets and transfected BHK fibroblasts indicated that the amount of immunoprecipitable GAD per BHK cell was well over 10-fold greater than that per human beta cell. Electrophoretic mobility of the native and recombinant GAD were identical. Immunoprecipitated GAD from transfected BHK cells migrated as two bands on one-dimensional reducing SDS-PAGE (as reported for islet-derived 64K; see Christgau et al., *J. Biol. Chem.* 286:21257–21264 (1991)). Stronger reducing conditions achieved by increasing βME from 1 to 5 to 15% or DTT from 0.05 to 0.2 to 0.5M appeared to convert the recombinant GAD to a single band corresponding to the most rapidly migrating species.

Each fluorogram contained $^{14}C$-labeled molecular weight markers (Amersham Corp.), three control lanes analyzing immunoprecipitations using positive control serum (PC), negative healthy control serum (NC), GAD-6 mouse monoclonal ascites, and up to 19 test sera. The positive control serum was obtained at onset from a diabetic child who is the Juvenile Diabetes Foundation (JDF) world standard for islet cell antibodies (ICA), tests positive for 64K antibodies (antibodies shown to precipitate a $M_r$ 64,000 protein band from radiolabeled human or other mammalian islets [Baekkeskov et al., *Nature* 298:167–169 (1982)]; the 64K protein was shown to be GAD [Baekkeskov et al., *Nature* 347:151–156 (1990)]) in isletbased assays, and has a moderate GAD65Ab level compared with the range seen in new-onset IDDM patients. (GAD65 antibodies are those that precipitate the recombinant human islet GAD, referred to as "GAD65." They are believed to be the same as the 64K antibodies.) GAD6 monoclonal antibody provides excess antibody binding capacity, and measures the maximum precipitable antigen per individual assay. Bands at Mr 64,000 were quantified by laser densitometric scanning as integrated area under each peak (2202 Ultroscan; LKB, Sweden) with threshold set at 8 (defining area $<1 \times 10^6$ as zero). Raw densitometry data, in arbitrary units measuring integrated area under densitometry curves, varied from 0 to $4.48 \times 10^7$ for unknowns, from 0 to $1.9 \times 10^6$ for the negative control (zero in seven out of nine films), from $0.4 \times 10^7$ to $3.3 \times 10^7$ for the positive diabetic control, and from $3.0 \times 10^7$ to $8.9 \times 10^7$ for the positive monoclonal control. Gels with film bands exceeding the densitometer sensitivity range were re-exposed for less time and rescanned. In all individual films, the positive diabetic control:negative control ratio was always >10:1, while the positive monoclonal control:negative control ratio was always >35:1. GAD65Ab index was calculated from integrated areas by the formula: index=(unknown−NC)/(PC−NC). Intra- and inter-assay coefficients of variation were 26 and 29% respectively. For qualitative results, any index above 0 was considered positive.

The immunoprecipitation assay showed linearity with respect to GAD65Ab amount over a range from 0.6 to 10 µl of a strongly reacting diabetic serum (FIG. 1, lanes 3–7). In these experiments, normal human serum was added to maintain Ig concentration equivalent to 10 µl serum. The assay also demonstrated linearity with respect to BHK-derived antigen concentration over a range of starting radioactivity from $2.5 \times 10^5$ to $2 \times 10^6$ cpm (FIG. 1, lanes 9–12), representing specific GAD65 radioactivity of $\sim 4 \times 10^3 - 3 \times 10^4$ cpm, from $\sim 15,000-120,000$ fibroblasts, respectively. Lane 13 shows reprecipitation of supernatant from the immunoprecipitation of lane 9, illustrating that the first reaction quantitatively precipitated all antigen.

Figure 2A:
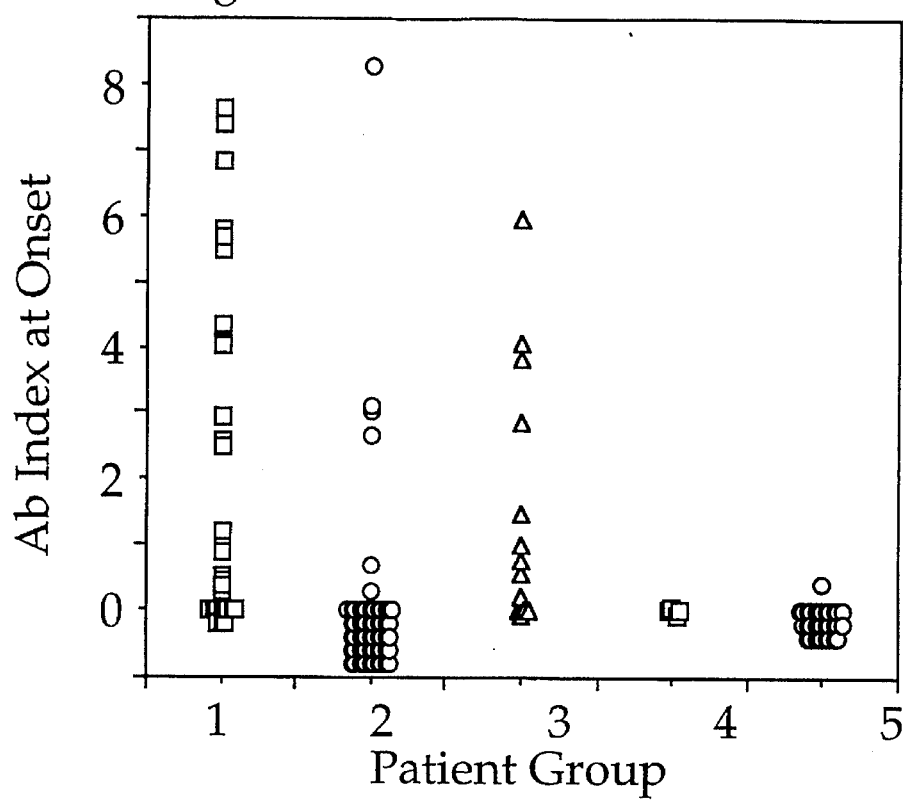
FIG. 2 illustrates the relationship of GAD autoantibodies to treatment regimen. (A) Quantitative GAD Ab indices in patients grouped by treatment type at 0 and 18 months after onset. (B) Treatment type at 18 months follow-up compared with GAD antibody positivity at onset.
Figure 2B:
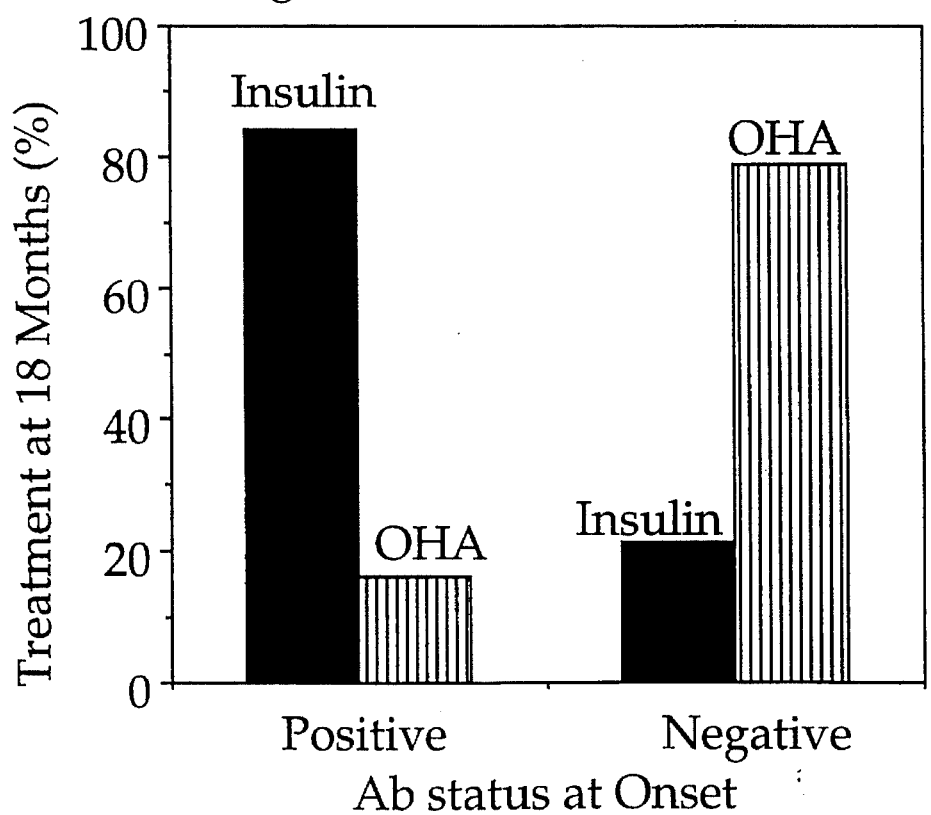

The GAD65Ab assay was used to analyze sera drawn at onset from the population-based sample of 120 diabetic patients grouped by treatment type at onset and 18 months later. The quantitative GAD65Ab index derived by densitometric scanning of fluorograms is shown for samples drawn at onset from each of the four diabetic treatment groups and for the healthy control group in FIG. 2A. There are clear differences in the GAD65Ab index between these groups, with a mean index ±SEM being 1.77±0.41, 0.29±0.15, 1.35±0.47, 0.012±0.013, and 0.013±0.013 for the five groups, respectively. Qualitative positivity in the five groups was 70, 10, 69, 20 and 3%, respectively. As shown in FIG. 2B, GAD65Ab at onset was strongly associated with insulin treatment 18 months later ($\chi^2=45$; P<0.0001). For example, 11 of 17 patients (65%) initially treated with oral agent, but with GAD65Ab at onset, required insulin treatment by 18 months while only 5 of 61 patients (8%) initially on oral agents, but without GAD65Ab at onset, later required insulin therapy ($\chi^2=26.0$; p<0.01). By 36 months after onset, three more GAD65Ab positive patients (total of 14 out of 17, 82%) required exogenous insulin.

Table 4 shows the prevalence of several clinical parameters (age, BMI, and family history), secretory function (fasting C-peptide), and antibody markers (ICA and GAD65Ab) in the four diabetic and one control groups. This table also estimates the ability of each of these criteria to detect group 3 patients among those in groups 2 and 3, and thus to predict insulin requirement in patients initially diagnosed with non-insulin-dependent diabetes (NIDDM). Although BMI, and especially C-peptide, also differ significantly between those requiring and not requiring insulin therapy, the ICA and GAD65Ab tests clearly have the best predictive value.

TABLE 4

Prevalence (Percent) of Clinical Parameters Such as Age, BMI, and Family History (FH); of Secretory Function Measured by Fasting C Peptide (Cpep); and of Antibody Markers Such as ICA and GAD65Ab, in the Four Diabetic and One Control Groups

| Group | Group 1 | Group 2 | Group 3 | Group 4 | Group 5 | Group 3 vs. groups 2 and 3* | | | | |
|---|---|---|---|---|---|---|---|---|---|---|
| treatment | I/I | O/O | O/I | I/O | Control | p ($X^2$) | Sens | Spec | PPV | NPV |
| Age < 35 | 24/37 (65) | 4/63 (6) | 5/16 (31) | 1/5 (20) | 12/33 (36) | 0.04 | 0.31 | 0.94 | 0.56 | 0.84 |
| BMI < 25 | 27/32 (84) | 9/61 (15) | 9/16 (56) | 2/5 (40) | 21/32 (66) | 0.008 | 0.56 | 0.77 | 0.39 | 0.87 |
| FH DM | 20/32 (63) | 33/59 (56) | 7/16 (44) | 3/5 (60) | 0/33 (0) | 0.39 | 0.44 | 0.44 | 0.18 | 0.74 |
| FH IDDM | 9/32 (28) | 14/59 (24) | 3/16 (19) | 0/5 (0) | 0/33 (0) | 0.78 | 0.19 | 0.76 | 0.04 | 0.78 |
| Cpep < 0.35 | 31/36 (86) | 10/63 (16) | 10/14 (71) | 0/5 (0) | ND | .0008 | 0.71 | 0.84 | 0.50 | 0.93 |
| ICA | 25/37 (68) | 5/63 (8) | 10/15 (67) | 0/5 (0) | 0/33 (0) | .0002 | 0.67 | 0.92 | 0.67 | 0.92 |
| GAD65Ab | 26/37 (70) | 6/63 (10) | 11/16 (69) | 1/5 (20) | 1/33 (3) | .0002 | 0.69 | 0.92 | 0.65 | 0.92 |

*Prediction of progression to insulin therapy (group 3) in patients initially diagnosed as NIDDM (groups 2 and 3). The observed prevalence of IDDM among newly diagnosed NIDDM patients was 16 of 181 (9%). $X^2$, Chi square test; Sens, sensitivity; Spec, specificity; PPV, positive predictive value; NPV, negative predictive value.

Figure 3A:
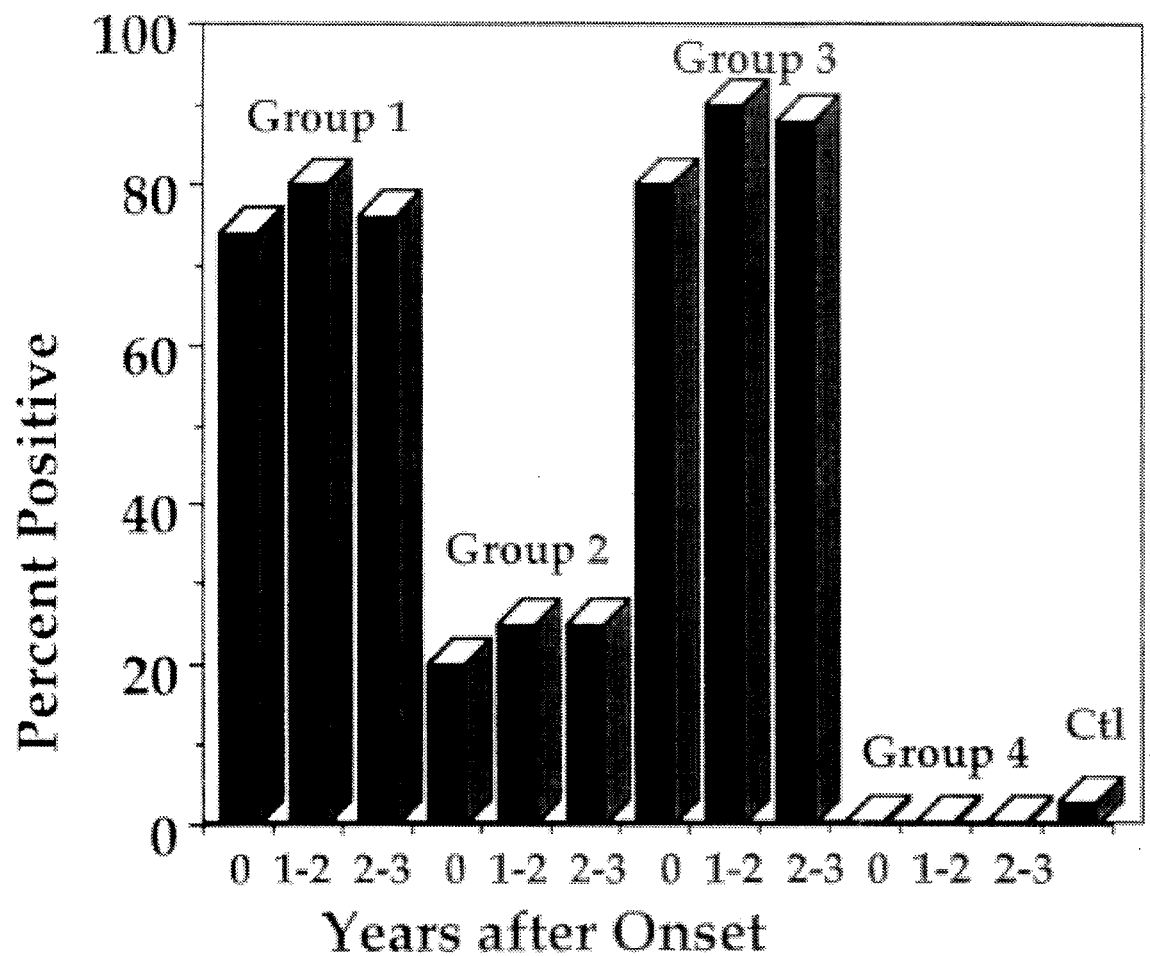
FIG. 3A shows qualitative GAD antibody positivity plotted by serum sampling time after onset and by treatment group in a subset of patients from whom multiple samples were drawn. Not every patient was sampled during every time interval.
Figure 3B:
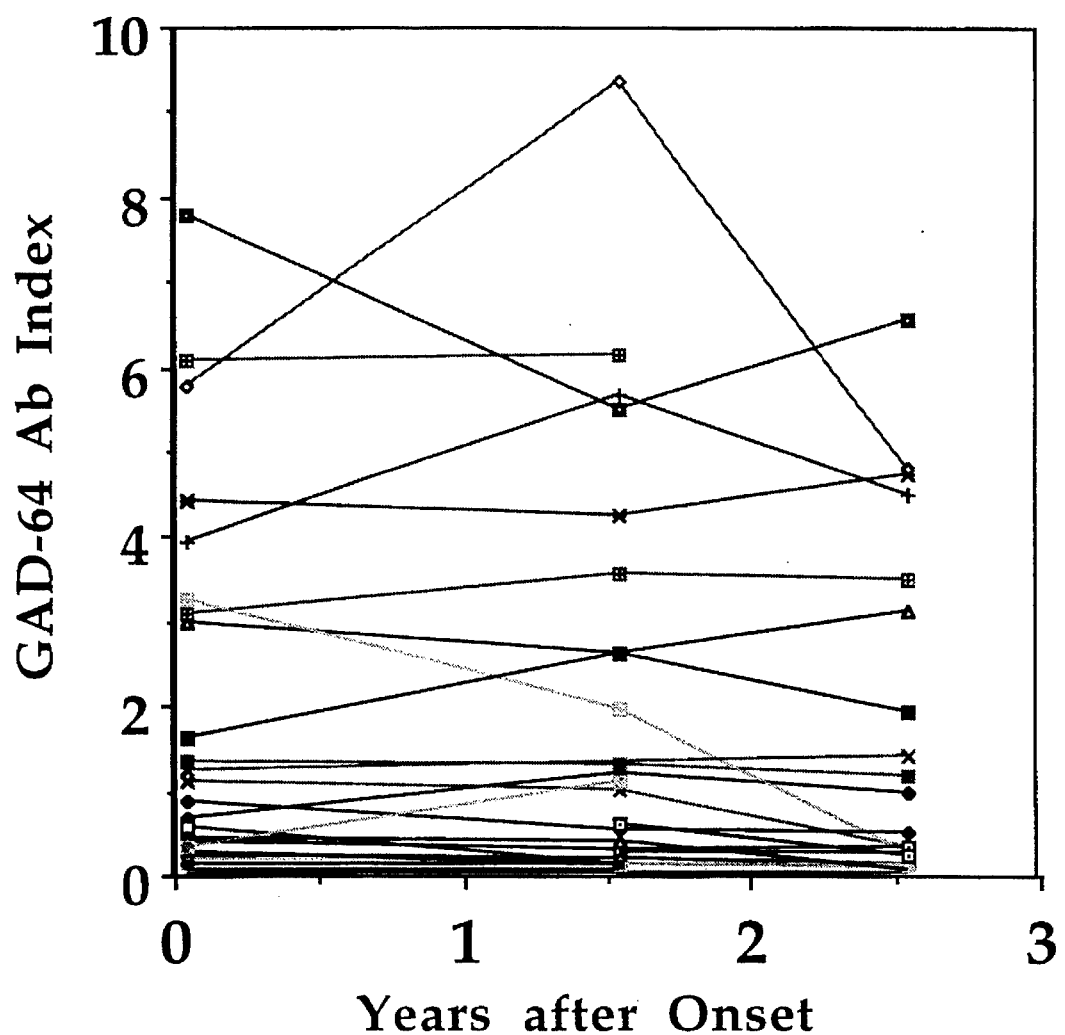
FIG. 3B shows the quantitative GAD antibody index at onset versus the index 1–2 and 2–3 years later for the 33 patients sampled in (3A). Each line represents a single patient.

In addition to serum obtained at onset, 48 patients had sera drawn once or twice more during the next 3 years. The percentage of GADAb positivity is summarized for each patient group and time interval in FIG. 3A. Qualitative GAD65Ab positivity in this subset was generally similar to that found in the onset samples from all patients (see FIG. 2A), although slightly higher in groups 2 and 4 due to small sample size. These data are shown primarily to establish the stability of GAD65Ab prevalence over time. In fact, 31 of 33 patients tested at multiple time points (94%) were always positive or always negative. Each line in FIG. 3B shows quantitative GAD65Ab levels in serial samples from the same patient during the three years after onset. Although some patients lost or gained autoantibody levels over time, most had remarkably stable GAD65Ab indices throughout the study.

Figure 3C:
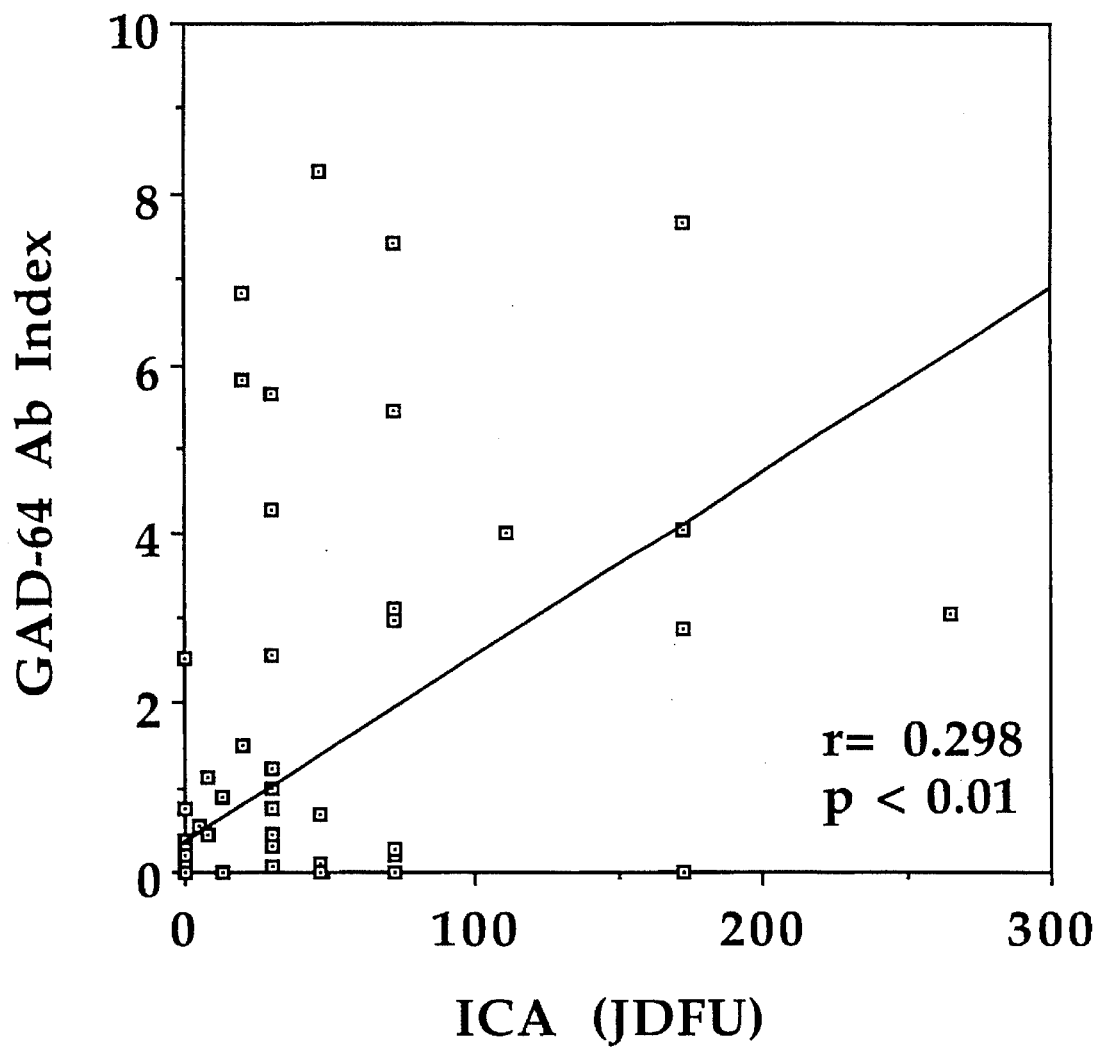
FIG. 3C is a plot of GAD Ab index versus ICA titer in JDF units.

Comparison of serum samples positive for GAD65Ab with those with ICA≧2JDF units (Table 5) reveals extensive qualitative concordance (93%) between the two tests. The few discordant sera are mostly GAD65Ab positive and ICA negative (7 of 153, 5%), perhaps due to the high sensitivity of the GAD immunoprecipitation assay, or in cases of high GADAb index, to variable expression of some GAD epitopes in standard ICA tissue sections. Other ICA antigens have been described (Gianani et al., *Diabetes* 41:347–353 (1992); Gillard et al., *J. Immunol.* 142:3826–3832 (1989); Karounos et al., *Autoimmun.* 6:79–91 (1991)), and it is not surprising that at least some sera (3 of 153, 2%) are ICA positive and GAD65Ab negative. However, as shown in FIG. 3C, plotting quantitative GAD65Ab index at onset (range 0–9.23) versus ICA titer at onset (range 0–5,520 JDF units) reveals limited but significant correlation between the two tests (r=0.298, P<0.01).

TABLE 5

Relationship of the Islet Cell Antibody Test to the GAD65Ab Test

| Group | Concordant | GAD+ ICA– | GAD index* | ICA+ GAD– | ICA JDFU* |
|---|---|---|---|---|---|
| 1 | 32/37 (86%) | 3/37 (8%) | 0.15, 2.51, 0.36 | 2/37 (5%) | 73, 13 |
| 2 | 62/63 (98%) | 1/63 (2%) | 0.27 | 0/63 (0%) | None |
| 3 | 13/15 (98%) | 1/15 (7%) | 0.21 | 1/15 (7%) | 47 |
| 4 | 4/5 (80%) | 1/5 (20%) | 0.06 | 0/5 (0%) | None |
| 5 | 32/33 (97%) | 1/33 (3%) | 0.42 | 0/33 (0%) | None |
| Total | 143/153 (93%) | 7/153 (5%) | Mean = 0.57 | 3/153 (2%) | Mean = 44 |

*For those positive for GAD65Ab alone, or for ICA alone, quantitative indices or JDFU titers, respectively, are shown.

The foregoing provides isolated and purified human islet cell GAD nucleotide sequences and recombinant human islet cell GAD polypeptides. These results offer, inter alia, a reproducible system to detect autoantibodies to the Mr 64,000 autoantigen in sera from patients with apparent non-insulin-dependent diabetes and thereby predict the clinical course of diabetes in these patients.

Although the foregoing invention has been described in some detail by way of illustration and example for purposes of clarity and understanding, it will be apparent that certain changes and modifications may be practiced within the scope of the appended claims.

We claim:

1. A method for predicting the clinical course of diabetes in a patient comprising:

testing a biological fluid selected from the group consisting of blood, plasma and serum from a patient diagnosed as having non-insulin-dependent diabetes for the presence of autoantibodies to human islet cell glutamic acid decarboxylase (GAD); and classifying said patient for clinical course of diabetes based on the presence or absence of said autoantibodies in said fluid.

2. A method according to claim 1 wherein said patient is further tested for:

(a) one or more additional diabetes-specific autoantibodies;

(b) C-peptide level; or (c) body mass index.

3. A method according to claim 1 wherein said patient is further tested for one or more additional diabetes-specific autoantibodies.

4. A method according to claim 3 wherein said one or more additional diabetes-specific autoantibodies are autoantibodies to antigens selected from the group consisting of insulin, carboxypeptidase H, p69 β-cell surface protein, sulfatide, 37 kDa tryptic fragment, 38 kDa β-cell component and p52 antigen.

5. A method according to claim 1 wherein the step of testing comprises:

combining the biological fluid with a labeled human islet cell GA under conditions suitable for immune complex formation;

separating immune complexes from uncomplexed GAD; and determining the presence of labeled GAD in said immune complexes.

6. A method according to claim 5 wherein said GAD is labeled with biotin or a radionuclide.

7. A method according to claim 5 wherein said GAD is a recombinant GAD.

8. A method according to claim 5 wherein said GAD has the amino acid sequence of SEQ ID NO: 2.

9. A method according to claim 5 wherein said determining step comprises measuring enzyme reaction, fluorescence, luminescence or radioactivity.

10. A method according to claim 5 wherein said determining step comprises detecting said immune complexes with a second antibody.

11. A method according to claim 5 wherein said separating step comprises binding said immune complexes to protein A.

12. A method for aiding in the diagnosis of incipient insulin-dependent diabetes in a patient by determining the presence of autoantibodies to human islet cell GAD comprising:

obtaining a sample of a biological fluid selected from the group consisting of blood, plasma and serum from a patient diagnosed as having non-insulin-dependent diabetes;

contacting said sample with a human islet cell GAD under conditions conducive to immune complex formation;

detecting the presence of immune complex formation between said GAD and autoantibodies to human islet cell GAD and determining therefrom the presence of autoantibodies to human islet cell GAD in said sample, wherein the presence of said autoantibodies indicates the existence of incipient insulin-dependent diabetes.

13. A method according to claim 12 wherein said GAD is labeled.

14. A method according to claim 13 wherein said GAD is labeled with biotin or a radionuclide.

15. A method according to claim 12 wherein said detecting step comprises separating immune complexes from the sample and determining the presence of labeled GAD in said complexes.

16. A method according to claim 12 wherein said GAD is a recombinant GAD.

17. A method according to claim 12 wherein said GAD has the amino acid sequence of SEQ ID NO: 2.

18. A method according to claim 12 wherein the GAD is attached to a solid phase.

19. A method according to claim 12 wherein said immune complex is detected by a second antibody.

20. A method according to claim 13 wherein said detecting step comprises measuring enzyme reaction, fluorescence, luminescence or radioactivity.

* * * * *